United States Patent [19]

Fioretti et al.

[11] Patent Number: 5,725,858
[45] Date of Patent: Mar. 10, 1998

[54] METHODS OF ENHANCING PRODUCTION PERFORMANCE OF BIRDS COMPRISING ADMINISTRATION OF HETEROLOGOUS PROTEIN COMPRISING AVIAN ALPHA-SUBUNIT INHIBIN PROTEIN

[75] Inventors: William C. Fioretti, Colleyville, Tex.; Konstantin Kousoulas, Baton Route; Daniel G. Satterlee, Prairieville, both of La.

[73] Assignees: Agritech Technologies, Ltd., Grand Prairie, Tex.; Board of Supervisors of Louisiana State Univ. and Agricultural & Mechanical College, Baton Rouge, La.

[21] Appl. No.: 481,633

[22] Filed: Jun. 7, 1995

Related U.S. Application Data

[63] Continuation-in-part of Ser. No. 395,554, Feb. 28, 1995, abandoned, which is a continuation-in-part of Ser. No. 202,964, Feb. 28, 1994, abandoned.

[51] Int. Cl.$^6$ .................... A61K 38/16; A61K 38/02
[52] U.S. Cl. .................... 424/192.1; 424/184.1; 424/185.1; 424/193.1; 424/195.11; 424/198.1; 514/2; 514/8; 514/12
[58] Field of Search .................... 514/2, 8, 12; 424/184.1, 424/185.1, 192.1, 193.1, 195.11, 198.1

[56] References Cited

U.S. PATENT DOCUMENTS

| 4,864,019 | 9/1989 | Vale et al. .................... 424/139.1 |
| 5,089,396 | 2/1992 | Mason et al. .................... 435/69.1 |
| 5,102,807 | 4/1992 | Burger et al. .................... 436/518 |

FOREIGN PATENT DOCUMENTS

WO 95/22980  8/1995  WIPO.

OTHER PUBLICATIONS

Daniel et al. Virology 202:540–549, 1994.
"Synthetic Peptide Segments of Inhibin α–and β–Subunits: Preparation and Characterization of Polyclonal Antibodies", Saito et al., *Endocrinology*, 1989, vol. 125, No.2, pp. 898–905.
Murdoch, W.J., "Immunoregulation of mammalian fertility," *Life Sci.*, vol. 55 (24), pp. 1871–1886 (1994).
Forage, R.G. et al., "Immunization against an inhibin subunit produced by recombinant DNA techniques results in increased ovulation rate in sheep." *J. Endocrinol.*, vol. 114 (2), p. R1–4 (Aug. 1987).
Morris, D.G. et al., "Effect of immunization against synthetic peptide sequences of the alpha N–subunit of bovine inhibin on ovulation rate, gonadotrophin concentrations and fertility in heifers." *J. Reprod. Fertil.*, vol. 103 (2), pp. 285–291 (Mar. 1995).
Bowie et al. 1990. Science 247–1306–1310.
Fraser et al., "Does inhibin have an endocrine role during the luteal phase of the primate menstrual cycle?", *Journal of Reproduction and Fertility*, No. 11, Abstract No. 78 (Jul. 1993).

Webley et al., "Inverse relationship between progesterone and inhibin α–subunit production by marmoset luteal cells *in vitro*", *Journal of Reproduction and Fertility*, No. 11, Abstract No. 155 (Jul. 1993).
Morris et al., "Effect of immunization against bovine inhibin peptides on FSH and LH in heifers", *Journal of Reproduction and Fertility*, No. 11, Abstract No. 156 (Jul. 1993).
Rivier et al., "Studies of the Inhibin Family of Hormones: A Review", *Hormone Res.*, vol. 28, pp. 104–118 (1987).
Akashiba et al., "Secretion of Inhibin by Chicken Granulosa Cells *in vitro*", *Poultry Science*, vol. 67, pp. 1625–1631 (1988).
Findlay, "An Update on the Roles of Inhibin, Activin, and Follistatin as Local Regulators of Folliculogenesis", *Biology of Reproduction*, vol. 48, pp. 15–23 (1993).
Johnson et al., "The molecular biology and endocrinology of inhibin in the domestic hen", *Journal of Endocrinology*, pp. 297–308, (1993).
Johnson et al., "Characterization of a Source and Levels of Plasma Immunoreactive Inhibin during the Ovulatory Cycle of the Domestic Hen", *Biology of Reproduction*, vol. 48, pp. 262–267 (1993).
Johnson et al., "Characterization and Quantitation of mRNA for the Inhibin α–Subunit in the Granulosa Layer of the Domestic Hen", *General and Comparative Endocrinology*, vol. 90, pp. 43–50 (1993).
Johnson et al., "Plasma Concentrations of Immunoeractive Inhibin and Gonadotropins following Removal of Ovarian Follicles in the Domestic Hen", *Biology of Reproduction*, vol. 49, pp. 1–6 (1993).
McNatty et al., "Contrations of immunoreactive inhibin in ovarian and peripheral venous plasma and follicular fluid of Booroola ewes that are homozygous carriers or non–carriers of the $Fec^B$ gene", *J. Reprod. Fert.*, vol. 95, pp. 489–502 (1992).
Rivier et al., "Age–Dependent Changes in Physiological Action, Content, and Immunostaining of Inhibin in Male Rates", *Endocrinology*, vol. 123, pp. 120–126 (1988).
Robertson et al., "Isolation of a 31 kDa form of inhibin from bovine follicular fluid", *Molecular and Cellular Endocrinology*, vol. 44, pp. 271–277 (1986).

(List continued on next page.)

*Primary Examiner*—David L. Fitzgerald
*Assistant Examiner*—Elizabeth C. Kemmerer
*Attorney, Agent, or Firm*—Jones & Askew

[57] ABSTRACT

The present invention relates, in general, to a method of enhancing the production performance of avians, by administering to a bird a heterologous protein comprised of inhibin protein, or a fragment thereof, and a carrier protein. The present invention also relates to a method of enhancing the production performance of avians, by administering to a bird a fusion gene product comprising a gene encoded for the expression of alpha-subunit avian inhibin protein, or a fragment thereof, and a gene encoded for the expression of a carrier protein. An effective amount of the heterologous protein or fusion gene product is administered to an animal such that an immunological response occurs in the animal against the heterologous protein. The present invention further relates to the above heterologous protein and fusion gene product, and to methods of producing the same.

20 Claims, 2 Drawing Sheets

OTHER PUBLICATIONS

Scanlong et al., "Active immunization of heifers against a synthetic fragment of bovine inhibin", *Journal of Reproduction and Fertility*, vol. 97, pp. 213–222 (1993).

Tsonis et al., "Inhibin bioactivity and pituitary cell mitogenic activity from cultured chicken ovarian granulosa and thecal/stromal cells", *Journal of Endocrinology*, vol. 116, pp. 293–299 (1988).

Glencross et al., "Effect of active immunization of heifers against inhibin on plasma FSH concentrations, ovarian follicular development and ovulation rate", *Journal of Endocrinology*, vol. 135, pp. 11–18 (1992).

Johnson, "Inhibin in the Hen", *Poultry Sciences*, vol. 72, pp. 955–958 (1993).

Meyer et al., "Antiserum to an inhibin alpha–chain peptide neutralizes inhibin bioactivity and increases ovulation rate in sheep", *J. Anim. Science*, vol. 69, pp. 747–754 (1991).

Morris et al., "Effect of immunizing prepuberal lambs of low and high ovulation rate genotypes with inhibin partially purified from bovine follicular fluid", *Theriogeneology*, vol. 35, No. 2, pp. 339–350 (Feb. 1991).

Morris et al., "Effect of immunization against synthetic peptide sequences of bovine inhibin α–subunit on ovulation rate and twin–calving rate in heifers", *Journal of Reproduction and Fertility*, vol. 97, pp. 255–261 (1993).

Risridger et al., "Current perspectives of inhibin biology", *Acta Endocrinologica (Copenh)*, vol. 122 pp. 673–682 (1990).

Wang et al., "Increase in Ovarian α–Inhibin Gene Expression and Plasma Immunoeractive Inhibin Level Is Correlated with a Decrease in Ovulation Rate in the Domestic Hen", *General and Comparative Endocrinology*, vol. 91, pp. 52–58 (1993).

Wang et al., "Complementary Deoxyribonucleic Acid Cloning and Sequence Analysis of the α–Subunit of Inhibin from Chicken Ovarian Granulosa Cells", *Biology of Reproduction*, vol. 49, pp. 1–6 (1993).

Wrathall et al., "Effects of active immunization against a synthetic peptide sequence of the inhibin α–subunit on plasma gonadotrophin concentrations, ovulation rate and lambing rate in ewes", *J. Reprod. Fert.*, vol. 95, pp. 175–182 (1992).

North et al., "Flock Recycling", *Commercial Chicken Production Manual*, Van Nostrand Reinhold, New york, pp. 434–439 (date unknown).

Chinnah et al., "Antigen dependent adjuncant activity of a polydispersed α–(1–4)–linked acetylated mannan (acemannan)", *vaccine*, vol. 10(8), pp. 551–557 (1992).

Chouljenko et al., "Expression and Purification of Chicken and Inhibition as a Fusion Protein with the E.Coli Maltose Binding Protein," *Poultry Science*, vol. 73 (Suppl. 1), p. 84 (1994).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 521 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..303

( x i ) SEQUENCE DESCRIPTION: SEQ ID NO:1:

```
CTG CAG CGC CCA TCG GAG GAC GTG GCC GCC CAC ACC AAC TGC CGC CGG    48
Leu Gln Arg Pro Ser Glu Asp Val Ala Ala His Thr Asn Cys Arg Arg
 1               5                  10                  15

GCG TCC CTC AAC ATC TCT TTC GAG GAG CTG GGC TGG GAC AAT TGG ATC    96
Ala Ser Leu Asn Ile Ser Phe Glu Glu Leu Gly Trp Asp Asn Trp Ile
             20                  25                  30

GTG CAC CCC AGC AGC TTC GTT TTC CAC TAC TGC CAC GGG AAC TGT GCC   144
Val His Pro Ser Ser Phe Val Phe His Tyr Cys His Gly Asn Cys Ala
         35                  40                  45

GAA GGC CAC GGG CTG AGC CAC CGG CTG GGG GTG CAG CTG TGC TGC GCC   192
Glu Gly His Gly Leu Ser His Arg Leu Gly Val Gln Leu Cys Cys Ala
     50                  55                  60

GCG CTG CCC GGC ACC ATG CGC TCA CTG CGT GTC CGC ACC ACC TCT GAT   240
Ala Leu Pro Gly Thr Met Arg Ser Leu Arg Val Arg Thr Thr Ser Asp
 65                  70                  75                  80

GGT GGC TAC TCC TTC AAG TAC GAG ACG GTG CCC AAC ATC CTG GCG CAG   288
Gly Gly Tyr Ser Phe Lys Tyr Glu Thr Val Pro Asn Ile Leu Ala Gln
                 85                  90                  95

GAC TGC ACC TGT GTC TAGCAGCTGG CATGCACGGC CAGACCGCG TGGATCTCCC    343
Asp Cys Thr Cys Val
                100

CGTTGCCTCT GGACTGCCCC AGTGCCAGAT GATGAGCCCA TCCCAGGGAT GGAGGAGTCA  403

CTCACACGGG CACTGCGCAG CCCGGAGCAG GGAGAGGGAC CCAGGTGGAA GTTTGGTGG   463

TGCCACCCTC CCTTTGACTG CCAGGGTTTC ATGGTTTCAG GTTGCGTGGG TGCTGCAG    521
```

( 2 ) INFORMATION FOR SEQ ID NO:2:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Leu Gln Arg Pro Ser Glu Asp Val Ala Ala His Thr Asn Cys Arg Arg
 1               5                  10                  15

Ala Ser Leu Asn Ile Ser Phe Glu Glu Leu Gly Trp Asp Asn Trp Ile
             20                  25                  30
```

-continued

| Val | His | Pro | Ser | Ser | Phe | Val | Phe | His | Tyr | Cys | His | Gly | Asn | Cys | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |
| Glu | Gly | His | Gly | Leu | Ser | His | Arg | Leu | Gly | Val | Gln | Leu | Cys | Cys | Ala |
|     | 50  |     |     |     |     | 55  |     |     |     |     | 60  |     |     |     |     |
| Ala | Leu | Pro | Gly | Thr | Met | Arg | Ser | Leu | Arg | Val | Arg | Thr | Thr | Ser | Asp |
| 65  |     |     |     |     | 70  |     |     |     |     | 75  |     |     |     |     | 80  |
| Gly | Gly | Tyr | Ser | Phe | Lys | Tyr | Glu | Thr | Val | Pro | Asn | Ile | Leu | Ala | Gln |
|     |     |     |     | 85  |     |     |     |     | 90  |     |     |     |     | 95  |     |
| Asp | Cys | Thr | Cys | Val |     |     |     |     |     |     |     |     |     |     |     |
|     |     |     |     | 100 |     |     |     |     |     |     |     |     |     |     |     |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CTCAGCCTGC TGCAGCGCCC      20

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GTGTCGACCG CGCGACGCCG AC      22

METHODS OF ENHANCING PRODUCTION PERFORMANCE OF BIRDS COMPRISING ADMINISTRATION OF HETEROLOGOUS PROTEIN COMPRISING AVIAN ALPHA-SUBUNIT INHIBIN PROTEIN

CROSS REFERENCE TO RELATED APPLICATIONS

This is a continuation-in-part application of U.S. patent application Ser. No. 08/395,554 filed Feb. 28, 1995, now abandoned, which is herein incorporated by reference, which is a continuation-in-part of U.S. patent application Ser. No. 08/202,964, filed Feb. 28, 1994, now abandoned, which is herein incorporated by reference.

FIELD OF THE INVENTION

The present invention relates, in general, to a method of enhancing the production performance of avians, by administering to a bird a heterologous protein comprised of inhibin protein, or a fragment thereof, and a carrier protein. The present invention also relates to a method of enhancing the production performance of avians, by administering to a bird a fusion gene product comprising a gene encoding for the expression of alpha-subunit avian inhibin protein, or a fragment thereof, and a gene encoding for the expression of a carrier protein. The present invention further relates to the above heterologous protein and fusion gene product, and methods of producing the same.

BACKGROUND OF THE INVENTION

Ratites are flightless, generally large, running birds, comprising several orders including the species Ostrich, Emu, Rhea, Cassowaries, and Kiwis. An emu (*Dromiceius novaehollandiae*) is an Australian ratite bird which is characterized by rudimentary wings and a feathered head and neck. An average adult emu is approximately 6 feet tall and weighs approximately 150 pounds. An ostrich (*Struthio camelius*) is a large running bird with small wings and thick powerful legs. A standard adult ostrich is approximately 8 feet tall and weighs approximately 325 to 375 pounds. The term "rhea" is the common name for members of the avian order Rheiformes. Rheiformes are an order of South American running birds, called American ostriches, which differ from the true ostrich in their smaller size, feathered head and neck, and three-toed feet among other features.

The ostrich and emu have long had a commercial value in their natural environments of South Africa and Australia, respectively. Ostrich products have been in demand for more than 100 years, and a substantial worldwide market exists for their hides, meat, and feathers. For example, ostrich leather is used in boots, handbags, jackets, attache cases, wallets, and many other articles. Ostrich feathers are used in fashion, costuming, and in feather dusters.

In contrast, the emu is a relative newcomer to the market place. It is valued for the same products with the addition of an essential oil that is used in the cosmetic industry. Emu oil, rendered from a thick layer of subcutaneous fat has deep penetrating properties which make the oil useful in cosmetic creams, such as, wrinkle retardant emollients. Also, possible medicinal uses for emu oil, such as the treatment of arthritis, are currently being investigated. A typical full-grown emu can achieve a height of 1.6 to 1.9 m or more, and weight 30 to 45 kg or more. Emus mature at about one year, and pre- and post-pubescent emus never show gender specific phenotypic differences. Similar to the ostrich, the emu population in the United States has also experienced explosive growth within the last several years. As of 1994, there were approximately 150,000 total emu, including 15,000 breeding pairs, in the United States. It is predicted that the numbers of emus in 1995 will further increase to between 500,000 and 750,000 birds, of which 45,000 are expected to be breeding pairs.

There is a growing demand for ratite products in several countries, including Australia, Belgium, Israel, Canada, the Netherlands, Namibia, South Africa, and Zimbabwe. Accordingly, over the past several years there has been explosive growth in the domestic market for ostrich and emu, and to a lesser extent rhea. In the last five years, the number of breeding ostrich pairs and total bird numbers in the United States has increased 7.5- and 20-fold, respectively. It is estimated that in 1995, 200,000 ostriches, including 20,000 breeding pairs, will exist in the United States. The tremendous interest in breeding these animals is due to the significant value of adults, as well as immature animals, and especially for proven breeding pairs of ostrich which are valued as high as $75,000.00, with an emu pair valued at $30,000.00 or more. Immature ostriches at three to four months of age are valued at approximately $7,500.00, and immature emu are valued at approximately $5,000.00. A majority of the animals are purchased between three and six months of age.

Further, there is tremendous interest in ratites as an alternative to more traditional forms of animal agriculture. Several factors relating to ratites make them a superior alternative to the more traditional forms of animal agriculture (i.e., beef cattle, swine and sheep farming). These factors include: superior feed conversion ratios, a greater ability to be intensively farmed, large animal size, enhanced reproductive capacity, and exceptional nutritional value of their meat.

For example, ostrich meat, which is a red meat resembling beef, contains significantly less fat, calories, and cholesterol than chicken or turkey meat. More particularly, an 85 gram portion of Ostrich meat contains 2 grams of fat, 58 mg of cholesterol, and 97 calories. In contrast, an 85 gram portion of turkey meat contains 3 grams of fat, 59 mg of cholesterol, and 135 calories. An 86 gram portion of chicken meat contains 3 grams of fat, 73 mg of cholesterol, and 140 calories. An 85 gram portion of beef (steak) contains 15 grams of fat, 77 mg of cholesterol, and 240 calories. And finally, an 85 gram portion of pork contains 19 grams of fat, 84 mg of cholesterol, and 275 calories. (Values for ostrich meat were derived from AMSI Quality Laboratory Report #0800100. Values for the other meats were derived from U.S.D.A. Handbook No. 8, "Nutritive Value of Foods".) Similar to the ostrich, emu meat is a low fat red meat. More particularly, a 100 gram portion of emu meat contains 1.7 g fat, 57.5 mg cholesterol, and 109 calories. (Values for emu meat were derived from Silliker Laboratories of Texas, Inc.)

Also, ratites such as ostriches provide approximately 100 pounds of meat at the age of 12 months and therefore produce a substantial amount of meat in a relatively short period of time.

An illustration of how ratites are a superior alternative to the more traditional forms of animal agriculture is the following comparison of an ostrich and a cow. First, an ostrich has a gestation or incubation period of 42 days, wherein a cow requires 280 days. Second, an average ostrich produces more than 20 offspring per year, whereas a cow produces one offspring per year. Third, the feed conversion ratio of an ostrich is less than 2:1 whereas the feed conversion ratio of a cow is 5:1. Fourth, the days from conception to slaughter is approximately 407 days for an ostrich in contrast to 645 for a cow. Finally, ostriches produce feathers in addition to their meat and leather, whereas cows do not produce products other than meat and leather.

Considering these attributes, and the increasing needs of the world population for meat which is nutritious yet low in fat and cholesterol and which may be efficiently produced with a minimum negative impact on the environment, the ratite industry has a high potential for future growth.

Currently, the demand for ratites far outweighs the supply. However, ratite producers are limited by sub-optimal egg production in most breeding age females. Depending on the species, most ratites in captivity currently lay an average of 10–20 eggs per year whereas their genetic potential for egg production is thought to exceed over 60 eggs per year. For example, a high-producing ostrich in the wild can lay an egg approximately every 48 hours during breeding season, and a high producing emu in the wild can lay an egg approximately every 72 hours in breeding season. In contrast, an ostrich in captivity often takes 5 to 10 days to lay an egg, and an emu often takes 4 to 8 days to lay an egg.

A slaughter market of ratites will not evolve until sufficient numbers of offspring are produced annually. According to some estimates, in order for a slaughter market to be maintained, there must be at least 250,000 animals available annually. Therefore, a method of enhancing production performance will greatly accelerate the growth of the market. Accordingly, there is a need for a composition and method of enhancing production performance in birds, and particularly in ratites such as ostriches and emus.

In addition to the newly emerging ratite industry, an enormous industry exists which encompasses the more established poultry species, primarily egg-type chickens (Single Comb White Leghorns), meat-type chickens (broilers), turkeys, ducks, geese, and quail. Worldwide demand for poultry meat and egg products is great and has been steadily increasing during the last decade.

The following is an attempt to characterize the size and complexity of the poultry meat industry in the USA, exclusive of ratite production. For purposes of this discussion, it should be understood that current population figures (U.S. Census, 1990 data) suggest that there are approximately 250 million inhabitants of this country. Furthermore, the population of America by the year 2000 is projected to be approximately 275 million people which represents an increase of 25 million people. From 1990 to 1995 (using U.S.D.A. projected figures for 1995), per capita consumption of broiler and turkey flesh averaged 76.7 and 18.1 pounds, respectively (See Anonymous, Poultry Processing Sourcebook, *Meat Processing*, Vol. 33(9): 22–25, (1994) and Bowman, M., Beef and Pork: Competing for the Food Dollar, *Meat Processing*, Vol. 33(12): 16–25, (1994)). This translates into an average total per capita poultry meat consumption of 94.8 pounds during the last 5 years.

Also documented is the steady trend of rising poultry meat consumption. For example, broiler per capita consumption has increased approximately 28 pounds (from 55.6 pounds in 1985 to 83.5 pounds in 1995). Likewise, turkey per capita consumption has risen approximately 2.5 pounds (from 15.9 pounds in 1989 to 18.4 pounds in 1995). This trend of increased consumption of chicken and turkey meat products is expected to continue in the future parallel to the anticipated growth in human population (See values cited above). If both predictions are correct, then by the year 2000, nearly 16.6 million tons of chicken and turkey meat will be consumed annually in this country alone. The trend of increased poultry consumption is directly related to the fact that poultry meats are considered to be "heart-healthy" foods (low in animal fat content) and pricewise, they favorably compete with the more expensive red-meats (such as beef, pork, and lamb).

Enhancing production performance of chicken and turkey breeder hens would therefore be of significant economic value to an industry currently enjoying high growth due to an ever increasing product demand. To satisfy consumer demand and maintain their competitive edge in meat pricing, broiler and turkey breeders will continue to be in the business of producing as many hatching eggs as possible. Therefore, any method capable of increasing egg production by even small amounts would generate significant economic benefits.

As an example, the scenario of a single broiler breeder hen (per hen housed basis) laying 15 additional eggs during one production cycle (approximately 1 year in length) is as follows. Such a case would, at current market chick prices ($0.16/chick), result in the generation of an extra $2.00 income from the sale of additional hatchlings and $10–12.00 as proceeds from the added sales of chicken meat generated from the grow-out of these chicks (after considering appropriate deductions for feed costs and fixed costs). Because the estimated broiler breeder hen population is believed to be in excess of 60 million hens in the United States, economic gain would be approximately $750+ million. Including the estimating monies that could be anticipated by enhancing production performance in turkey breeders (as well as in hens comprising the specialized poultry businesses of ducks, geese and quail, and including the chickens discussed above) it is conservatively estimated to be between $1–2 billion for the overall economic gain that might be realized from the meat-side of the poultry industry, including all poultry raised for consumption of flesh, excluding ratites.

It should be noted that the poultry industry first developed in this country as primarily a table egg industry. When fowl were subsequently selected for enhanced body weight (meat-type chickens), such genetic selection had deleterious effects on egg production rates. In other words, egg production proved to be negatively correlated with the genetic change found after selection for increased body weight. Therefore, the potential to enhance production performance in broiler and turkey breeder hens (meat-type birds) via endocrine manipulation (such as is contemplated in the present invention) should be greater in meat-type birds than in Single Comb White Leghorns, birds bred for intensity of egg production since the late 1920s. On the other hand, there are 3 to 4 times as many table egg layers, as discussed below, than broiler breeder birds in America. Therefore, even very small enhancements in production performance in egg-type birds are greatly magnified when one considers the size of the bird populations that can be affected.

The following is a discussion of the size and importance of the table egg industry in this country. Per capita consumption of eggs has remained reasonably stable from 1989 to 1992 and ranged between 30.0 to 30.4 pounds (See Table 653: Per capita consumption of major food commodities, Unites States, 1984–92, *Agricultural Statistics*, 1993, U.S.D.A. Natl. Agri. Stat. Ser., U.S. Govt. Printing Office, Washington, D.C., p. 457; 1993 and 1994 data unavailable). Stagnant table egg consumption rates in America are likely directly associated with public concern with consumption of egg yolks which are perceived to be high in cholesterol content.

Despite stable per capita egg consumption rates, the numbers of table egg layers have steadily increased from 228.8 million hens in 1990 to 240.7 million hens in 1994 (See Bell, D. D., *University of California Monthly Statistical Report*, Table 28: Table egg layers: Number on farms during month, 1980–93, UC Riverside). This trend of increasing numbers of laying hens may simply reflect a need for more eggs to satisfy increased population numbers, increased export of eggs and egg products, or yet other unidentified factors. Whatever the reason, because almost 80% of the world's eggs are produced outside the Americas, this suggests that any positive effects that can be realized within the United States table egg market may be multiplied by a factor of five to achieve worldwide economic significance. However, if one restricts calculations solely to the United States, and one holds per capita consumption steady at approximately 30.2 pounds, and accepts the projection that our population will increase to 275 million people in the next 5 years, then by the year 2000, nearly 4.2 million tons of chicken eggs will be produced annually in this country alone.

A dollar value for the enhancement of egg production in table egg layers is difficult to derive due to the existence of many complex features of a Leghorn's production cycle that affect decision making (e.g., cost of replacement pullets versus the use of molting, deleterious effects of molting on post-molt performance, loss of egg sales during molting, etc.). However, it would not be unreasonable to conclude that an increase in egg lay in egg-type chickens, on a per hen housed basis of only half the magnitude of that discussed above for broiler breeders, would translate into at least a multi-million dollar economic benefit.

The phrase "enhancing production performance" is understood by those of ordinary skill in the art to denote an increase in one or more of the following in female birds: accelerated onset of egg lay; accelerated onset of maximum egg production; prolonged persistence of egg lay; increased intensity of egg lay; or increased total lifetime egg lay. The phrase also includes improved feed conversion ratios; improved egg shell quality; or improved resistance to adverse laying conditions such as heat stress, overcrowding, poor nutrition, and noise. The phrase means an increase in one or more of the following in males: accelerated onset of puberty or production of sperm; accelerated onset of maximum sperm production; increased persistence of sperm production; increased intensity of sperm production (sperm count); increased ejaculate volume; improved sperm viability; increased testosterone production; or increased libido.

Recently, the hormone inhibin has been studied as a potential means for increasing ovulation in mammals. Inhibin is a peptide hormone primarily produced by the gonads, and more particularly by growing follicles and testes. In mammals, it functions as an inhibitory feedback regulator of pituitary follicle-stimulating hormone ("FSH") secretion. While inhibin's existence was first postulated over 60 years ago, its chemical isolation was only recently achieved.

Mammalian inhibin is a dimeric protein hormone which is composed of an α-subunit (molecular weight 18,000) and a β-subunit (molecular weight 14,000). The α-subunit is unique to inhibin as dimers of the β-subunit form activin, a hormone which releases FSH from the pituitary gland. The β-subunit exists in two forms ($\beta_A$ and $\beta_B$), which are distinct but quite similar. Therefore, depending on the β-subunit involved, inhibin exists as inhibin-A or inhibin-B. Both subunits α and β, when joined by disulfide bonds, are required for biological activity in suppressing follicle-stimulating hormone ("FSH") secretion from the pituitary. The amino acid sequence of the α-subunit of inhibin exhibits approximately 80–90% similarity among the porcine, bovine, human, murine, and domestic chicken species. Excellent reviews on the isolation, production, assay, and biological actions of inhibin are available in Risbridger et al., Current Perspectives of Inhibin Biology, *Acta Endocrinologica (Copenh)*, 122:673–682, (1990); and Rivier, C., et al., Studies of the Inhibin Family of Hormones: A Review, *Hormone Research*, 28:104–118 (1987), which are hereby incorporated by reference.

In mammals and birds, FSH plays a role in follicular growth and development, while luteinizing hormone ("LH") is believed to induce ovulation. Several brain and gonadal factors (peptide and steroid hormones) interact to control gonadotropin hormone release. Of these factors, gonadotropin-releasing hormone ("GnRH") and inhibin exert opposite controls on pituitary FSH secretion in mammals. Gonadotropin-releasing hormone is a brain decapeptide which acts to stimulate FSH and LH secretion, while inhibin is a gonadal protein which apparently acts to selectively inhibit FSH secretion in mammals.

A basic knowledge of the avian ovulatory process is needed to understand the role of inhibin in the endocrine control of ovulation in birds. Growing follicles on the functionally mature ovary of the domestic hen exist in a distinct size hierarchy. A typical ovary contains four to six large, two to four centimeter in diameter, yolk-filled follicles ($F_1$ to $F_4$, $F_6$), accompanied by a greater number of smaller, two to ten millimeter, yellow follicles, and numerous very small white follicles. The largest preovulatory follicle ($F_1$) is destined to ovulate the next day, the second largest ($F_2$) on the following day (approximately 26 hours later), and so on. The control of follicular recruitment and development within this hierarchy is poorly understood. Pituitary gonadotropin involvement has been proven, yet the role of inhibin in the control of avian gonadotropin secretion and control of ovulation remains unclear.

A recent strategy to induce hyper-ovulation in mammalian species has been the development of methods which involve neutralization of endogenous inhibin activity. For example, the active immunization of mammals against various inhibin-containing compounds has been studied. Immunoneutralization of inhibin has been associated with increased ovulation rates in heifers, sheep, gilts, and rats.

Accelerated ovulation rates found in mammals vaccinated with antigenic inhibin preparations is thought to be a consequence of elevated plasma FSH levels which lead to enhanced ovarian follicular development. A variety of antigens have been used as vaccines in studies which demonstrated an elevation in ovulation rate of mammals. Some of the antigens tested in mammals include: recombinant DNA derived fragments of the inhibin α-subunit (Wrathall et al., Effects of active immunization against a synthetic peptide sequence of the inhibin α-subunit on plasma gonadotrophin concentrations, ovulation rate and lambing rate in ewes, *J. Reprod. Fert.*, 95:175–182, 1992; and Meyer et al., Antiserum to an Inhibin Alpha-Chain Peptide Neutralizes Inhibin Bioactivity and Increases Ovulation Rate in Sheep, *Scientific Journal Series of the Minnesota Agric. Exp. Sta.*, paper No. 17,103, 1991), synthetic peptide replicas of the N-terminal sequence of bovine inhibin α-subunit coupled to ovalbumin (Glencross et al., Effect of active immunization of heifers against inhibin on plasma FSH concentrations, ovarian follicular development and ovulation rate, *Journal of Endocrinology*, 134, 11–18, 1992), synthetic peptide sequences of bovine inhibin α-subunit conjugated to human serum albumin (Morris, et al., Effect of immunization against synthetic peptide sequences of bovine inhibin α-subunit on ovulation rate and twin-calving rate in heifers, *Journal of Reproduction and Fertility*, 97:255–261, 1993), and partially purified inhibin from bovine follicular fluid (Morris et al., Effect of Immunizing Prepuberal Lambs of Low and High Ovulation Rate Genotypes with Inhibin Partially Purified From Bovine Follicular Fluid, *Theriogenology*, Vol. 35 No. 2, 1991).

Despite conflicting data on how levels of FSH fluctuated during the ovulatory cycle, in all cycling mammals studied, immunoneutralization of endogenous inhibin consistently enhanced ovarian follicular development and ovulation rate, regardless of the antigen used or the mammalian species challenged.

As stated above, inhibin involvement in the regulation of reproductive function in avian species remains unclear. Thus far, published reports have been restricted to the reproductive function of inhibin in domestic fowl. The bulk of this literature supports the theory that inhibin likely exerts parallel physiological roles in fowl to those documented in mammals: in hens, inhibin may serve as a regulator of follicular recruitment and/or development. However, in birds, inhibin's involvement in the control of ovulation rate may or may not be through suppression of pituitary FSH secretion. For example, although low egg producing hens have been found to have higher levels of inhibin in plasma and the granulosa cell layers of preovulatory follicles than high egg producing hens, no difference has been found in plasma FSH levels associated with the rate of egg laying. Wang et al., Increase in Ovarian α-Inhibin Gene Expression and Plasma Immunoreactive Inhibin Level is Correlated with a Decrease in Ovulation Rate in the Domestic Hen, *General and Comparative Endocrinology*, 91, 52–58, (1993). This reference, therefore, suggests that in hens the ovulation rate-related changes in inhibin α-subunit gene expression and plasma immunoreactive inhibin levels do not directly affect ovulation rate through a modulation of plasma FSH levels. Further, in Johnson, P. A., Inhibin in the Hen, *Poultry Science*, 72:955–958, (1993), a bovine inhibin RIA system was used to successfully assess immunoreactive inhibin in the plasma of hens, however no significant peak of immunoreactive inhibin was detected throughout the ovulatory cycle in spite of a preovulatory surge of LH. Accordingly, the role of inhibin in folliculogenesis in birds remains unclear.

Recently, the α-subunit of chicken inhibin was successfully cloned and sequenced. Wang and Johnson, Complementary Deoxyribonucleic Acid Cloning and Sequence Analysis of the α-Subunit of Inhibin from Chicken Ovarian Granulosa Cells, *Biology of Reproduction*, 49, 1–6, (1993), which is incorporated herein by reference in its entirety. Comparison of the avian inhibin sequence to known mammalian inhibin α-subunit sequences showed an 86–89% homology. Northern blot analysis using two isolated probes (cINA$_6$ and cINA$_{12}$) revealed that the inhibin α-subunit is expressed in chicken ovarian granulosa cells but not in chicken brain, kidney, liver or spleen tissues.

Therefore, the biology of inhibin in birds remains poorly understood, and the responses of birds to challenges with antigenic inhibin has not yet been attempted or monitored. Accordingly, as the ratite market is substantially limited by the sub-optimal production performance of many ostriches, emus, and rhea, what is needed is a composition and method for enhancing the production performance of these birds.

Further, the improvement of the production performance of all poultry is needed to increase the amount of poultry produced for consumption and to improve the efficiency of such production, or feed conversion ratio. Accordingly, there remains a need for a composition and method of improving or enhancing production performance for all poultry, including chickens, turkeys, ducks, quail, and geese, among others.

There also is a need for a composition and method of enhancing production performance in exotic birds, such as the Psittaciformes. Psittaciformes include parrots, and are a monofamilial order of birds that exhibit zygodactylism and have a strong hooked bill. A parrot is defined as any member of the avian family Psittacidae (the single family of the Psittaciformes), distinguished by the short, stout, strongly hooked beak.

The need for a composition and method for enhancing production performance is not limited to birds. There remains a need for an effective composition and method for enhancing production performance in many animals. For example, there is a continued need for enhancing production performance in most animals that are raised agriculturally, such as pigs, cows, and sheep. There is also a continued need of enhancing production performance in fur bearing animals such as mink, fox, otter, ferret, raccoons, and in rodents such as rats, mice, gerbils, and hamsters used as pets and as laboratory research subjects, and there is an increased need for other animals whose hides are used for decorative purposes.

Also, a composition and method for enhancing production performance is also needed to increase the population of many animals such as exotic or endangered species to avoid their extinction. There is further a continued need for enhancing production performance in animals used for racing, entertainment, or showing (competitions) such as horses, dogs, cats, zoo animals, and circus animals. As shown by the increased demands for infertility treatment of humans, there is also a need for enhancing production performance in humans. Accordingly, there remains a need for a composition and method for enhancing production performance in many animals.

SUMMARY OF THE INVENTION

The present invention relates, in general, to a method of enhancing the production performance of animals, by administering to the animal a heterologous protein comprised of inhibin protein, or a fragment thereof, and a carrier protein. The present invention also relates to a method of enhancing the production performance of animals, by administering to the animal a fusion gene product comprising a gene encoding for the expression of alpha-subunit inhibin protein, or a fragment thereof, and a gene encoding for the expression of a carrier protein. An effective amount of the heterologous protein or fusion gene product is administered to an animal such that an immunological response occurs in the animal against the heterologous protein. It is to be understood that the method of the present invention enhances production performance of animals that produce inhibin. Preferably, the animal is a bird. More preferably, the bird is a chicken. Another preferred bird is a ratite, such as, an emu, an ostrich, a rhea, or a cassowary.

The present invention further relates to the above heterologous protein and fusion gene product, and to methods of producing the same. More particularly, the present invention is directed to a composition and method for making a heterologous protein comprising inhibin, or a fragment thereof, and a carrier protein. The inhibin protein, or fragment thereof, can be avian inhibin, mammalian inhibin, piscine inhibin, or reptilian inhibin. The carrier protein, includes, but is not limited to, maltose binding protein, thyroglobulin, keyhole limpet hemocyanin, or bovine serum albumin, among others. The preferred carrier protein is maltose binding protein.

The heterologous protein can be either inhibin conjugated to the carrier protein or inhibin fused to the carrier protein. The method of producing the fused heterologous protein comprises inserting cDNA which is encoded for expressing inhibin, or a fragment thereof, into a vector which contains coding information for the production of a carrier protein. After inserting the vector into an expression system, the fused heterologous protein is expressed by the system. Preferably, the heterologous protein is comprised of ratite inhibin, such as ostrich inhibin, emu inhibin, and rhea inhibin. Another preferred heterologous protein is comprised of chicken inhibin.

The present invention is also directed to a method of enhancing production performance in animals via the administration of the heterologous protein of the present invention which comprises inhibin protein, or a fragment thereof, and a carrier protein. In one embodiment, the method comprises administering an effective amount of the protein to a female animal. In another embodiment, the method comprises administering an effective amount of the protein to a male animal. Preferably, an immunological response occurs in the animal directed against the heterologous protein. More preferably, the immunological response which occurs in the animal is also directed against the inhibin protein produced by the animal (endogenous inhibin).

The present invention is also directed to a fusion gene product comprising a gene encoded for the expression of alpha-subunit inhibin protein, or a fragment thereof, and a gene encoded for the expression of a carrier protein. The gene encoded for the expression of inhibin protein, or fragment thereof, may be encoded to express avian inhibin, mammalian inhibin, piscine inhibin, or reptilian inhibin. The gene encoded for the expression of a carrier protein may be encoded to express maltose binding protein or bovine serum albumin, among others. The preferred gene encoded to express a carrier protein is encoded to express maltose binding protein.

The present invention also relates to a method of enhancing the production performance of animals, by administering to the animal a fusion gene product comprising a gene encoded for the expression of alpha-subunit inhibin protein, or a fragment thereof, and a gene encoded for the expression of a carrier protein. More particularly, the present invention further encompasses gene therapy methods whereby DNA sequences encoding inhibin, or fragments thereof, and a carrier protein are introduced into an animal. The fusion gene product of the present invention may be administered directly to the animal, or it may be administered in a vector, or in a cell containing a vector having the fusion gene product therein.

The method of the present invention enhances production performance in female animals which produce inhibin, such as mammals, reptiles, fish, and birds. More particularly, this method enhances production performance in female galliformes and ratites. More particularly, this method enhances production performance in chickens, turkeys, ostriches, emus, and rhea. This method also enhances production performance in turtles, including endangered turtle species. Unexpectedly, the method of the present invention increases the onset of puberty or egg lay in animals. Also, the method of the present invention unexpectedly accelerates the onset of maximum egg lay in an animal. Further, the method of the present invention increases the intensity of egg lay of an animal. Further still, the method of the present invention surprisingly prolongs the persistence of maximum egg lay in animals. Still further, the method unexpectedly increases the lifetime total egg lay of an animal. In avians, the method of the present invention also improves the feed conversion ratio of a bird. Also, the method of the present invention unexpectedly reduces or eliminates the effect of adverse laying conditions on egg lay rates of animals exposed to such conditions. Such adverse conditions include elevated temperatures, overcrowding, poor nutrition, and noise.

Surprisingly, the method of the present invention also improves production performance in male animals which produce inhibin, such as mammals, reptiles, and birds. More particularly, the method of the present invention increases testosterone levels in male animals. Similarly, the method of the present invention increases the onset of puberty or sperm production in male animals. Also, the method of the present invention accelerates the onset of maximum sperm production in a male animal. Further, the method of the present invention unexpectedly increases the intensity of sperm production (sperm count) by a male animal. Further still, the method of the present invention prolongs the persistence of maximum sperm production in animals. Also, the method improves sperm viability in animals. Still further, the method unexpectedly reduces or eliminates the effect of adverse conditions on sperm production of animals exposed to such conditions. Such adverse conditions include elevated temperatures, overcrowding, poor nutrition, and noise. The method of the present invention also surprisingly increases the libido, and therefore, the reproductive potential, of a male bird.

As stated above, the method of the present invention is used to enhance production performance of any animal that produces inhibin, including, but not limited to, most animals that are raised agriculturally, such as pigs, cows, sheep, turkeys, quail, ducks, geese, chickens, and fish; in fur bearing animals such as mink, fox, otter, ferret, rabbits and raccoon; laboratory animals such as rats, mice, gerbils, and guinea pigs; for animals whose hides are used for decorative purposes such as alligators and snakes; exotic or endangered species; animals used for racing, entertainment, or showing (competitions) such as horses, dogs, cats, zoo animals, and circus animals; and humans. Additional avians that the method of the present invention enhances production performance thereof include ratites, psittaciformes, falconiformes, piciformes, strigiformes, passeriformes, coraciformes, ralliformes, cuculiformes, columbiformes, galliformes, anseriformes, and herodiones. More particularly, the method of the present invention may be used to enhance production performance of an ostrich, emu, rhea, chicken, turkey, ducks, geese, quail, partridge kiwi, cassowary, parrot, parakeet, makaw, falcon, eagle, hawk, pigeon, cockatoo, song bird, jay bird, blackbird, finch, warbler, canary, toucan, mynah, or sparrow.

Accordingly, it is an object of the present invention to provide an inhibin composition which induces an immunological response in an animal upon its administration to an animal.

It is yet another object of the present invention to provide a heterologous protein comprising inhibin protein, or a fragment thereof, and carrier protein.

It is a further object of the present invention to provide a composition comprising a fused heterologous protein comprised of inhibin, or a fragment thereof.

It is further an object of the present invention to provide a method for producing a fused heterologous protein comprising inhibin protein, or a fragment thereof, and a carrier protein.

It is yet another object to provide a fusion gene product comprising a gene encoded for the expression of alpha-subunit inhibin protein, or a fragment thereof, and a gene encoded for the expression of a carrier protein.

It is a further object of the present invention to produce an immunological response directed against the heterologous protein of the present invention by direct injection of the fused gene product of the present invention into an animal.

Yet another object of the invention is to provide compositions and methods useful for gene therapy for the modulation of inhibin levels.

It is another object of the present invention to provide a method for enhancing production performance in animals.

It is an object of the present invention to provide a method for enhancing production performance in birds.

It is a further object of the present invention to provide a method for enhancing production performance in ratites.

It is also an object to provide a method for enhancing production performance in chickens.

It is yet another object to provide a method for enhancing production performance in reptiles.

Is another object of the present invention to provide a method for enhancing production performance in mammals.

Is another object of the present invention to provide a method for enhancing production performance in fish.

It is further an object of the present invention to provide a method for enhancing production performance in humans.

These and other objects, features and advantages of the present invention will become apparent after a review of the following detailed description of the disclosed embodiments and the appended claims.

BRIEF DESCRIPTION OF THE DRAWINGS

FIG. 2 is a graphic representation of the data in Example 8.

DETAILED DESCRIPTION

Figure 1:
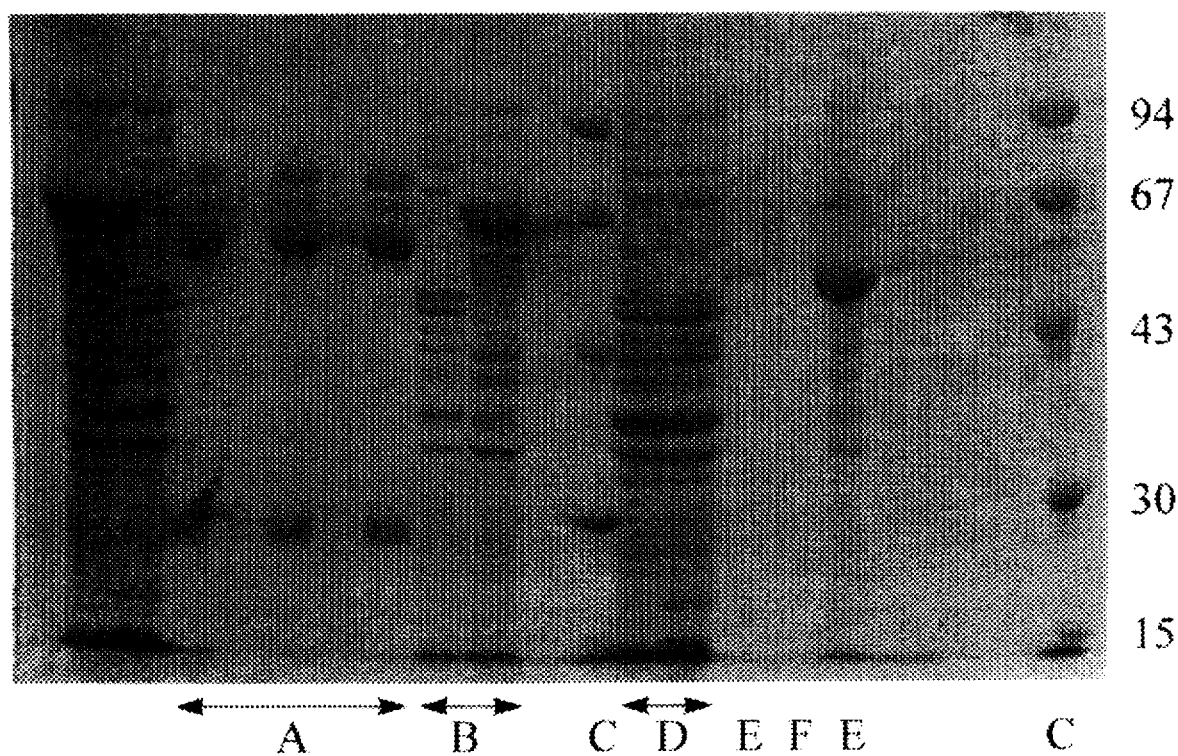
FIG. 1 is an SDS-PAGE gel wherein A is ostrich anti-(chicken inhibin-maltose binding protein) antibodies, B is plasmid pMAL™-c vector standard, C is protein molecular weight standards, D is the actual pMAL™-c vector used in the preparation of the fused heterologous protein, E is the purified fused chicken inhibin-maltose binding protein (heterologous protein) of the present invention, and F is eluent from a purification that was not loaded with the heterologous protein.

The present invention relates, in general, to a method of enhancing the production performance of animals, by administering to the animal a heterologous protein comprised of inhibin protein, or a fragment thereof, and a carrier protein. The present invention also relates to a method of enhancing the production performance of animals, by administering to the animal a fusion gene product comprising a gene encoded for the expression of alpha-subunit inhibin protein, or a fragment thereof, and a gene encoded for the expression of a carrier protein.

An effective amount of the heterologous protein or fusion gene product is administered to an animal such that an immunological response occurs in the animal against the heterologous protein. It is to be understood that the method of the present invention enhances production performance of animals that produce inhibin. Preferably, the animal is a bird. More preferably, the bird is a chicken. Mother preferred bird is a turkey. Yet another preferred bird is a ratite, such as, an emu, an ostrich, a rhea, or a cassowary. The present invention further relates to the above heterologous protein and fusion gene product, and to a method of producing the same.

After the following definitions, the composition of the present invention is described in detail, followed by a detailed description of the methods of the present invention.

Definitions

The term "bird" or "fowl," as used herein, is defined as a member of the Aves class of animals which are characterized as warm-blooded, egg-laying vertebrates primarily adapted for flying. The term "Ratite," as used herein, is defined as a group of flightless, mostly large, running birds comprising several orders and including the emus, ostriches, kiwis, and cassowaries. The term "Psittaciformes", as used here, include parrots, and are a monofamilial order of birds that exhibit zygodactylism and have a strong hooked bill. A "parrot" is defined as any member of the avian family Psittacidae (the single family of the Psittaciformes), distinguished by the short, stout, strongly hooked beak. The term "chicken" as used herein denotes both chickens used for egg production, such as Single Comb White Leghorns, and chickens raised for consumption, or broilers.

The term "egg" is defined herein as a large female sex cell enclosed in a porous, calcarous or leathery shell, produced by birds and reptiles. "Egg production by a bird or reptile", as used herein, is the act of a bird laying an egg, or "oviposition". The term "ovum" is defined as a female gamete, and is also known as an egg. Therefore, egg production in all animals other than birds and reptiles, as used herein, is defined as the production and discharge of an ovum from an ovary, or "ovulation". Accordingly, it is to be understood that the term "egg" as used herein is defined as a large female sex cell enclosed in a porous, calcarous or leathery shell, when it is produced by a bird or reptile, or it is an ovum when it is produced by all other animals.

The terms "onset of egg lay", "first egg lay" and "puberty", in reference to birds are used interchangeably herein, and denote when a bird lays its first egg. Accordingly, "accelerating the onset" of egg lay or puberty in avians, as used herein, denotes inducing an earlier date of first egg lay than a bird would normally have. Similarly, "puberty" and "onset of sperm production" in males are used interchangeably.

The phrases "enhancing production performance", "improving production performance" and "increasing production performance" are used interchangeably to denote an improvement in one or more of the following areas: accelerated onset of puberty (egg lay or ovulation in females; sperm production in males); accelerated onset of maximum egg lay or ovulation in females or accelerated onset of maximum sperm production in males; increased intensity of production of eggs in females, or of sperm in males; prolonged persistence of egg lay in females or of sperm production in males; increased total lifetime egg lay or ovulation in females; improved feed conversion ratios; improved egg shell quality; improved resistance to adverse conditions such as elevated temperatures, overcrowding, poor nutrition, and noise; improved sperm viability in males; increased testosterone production in males; increased ejaculate volume; and increased libido in males.

The phrase "intensity of egg lay" is known to those of ordinary skill in the art to denote frequency of egg lay.

The phrase "lifetime total egg lay" of a bird is defined as the total number of eggs laid by a bird during its entire life span. The phrase "hen day egg production" or "HDEP", as used herein, is defined as the number of eggs laid by a particular group of hens per day.

The phrase "accelerated onset of maximum egg lay" or "accelerated onset of maximum egg production" as used herein, denotes that the period of time from birth to when the animal lays eggs or ovulates at 50% of its peak lay rate or ovulation rate, is shorter than the normal period of time from birth to maximum egg lay.

It is to be understood that a method of "decreasing cholesterol levels" of an egg, as used herein, denotes a method of inducing a bird to lay one or more eggs having a lower cholesterol content than the average cholesterol content of eggs laid by birds of the same species.

In contrast to the term bird or fowl, the term "mammal", as used herein, is defined as a member of the class Mammalia which is a large class of warm-blooded vertebrates containing animals characterized by mammary glands, a body covering of hair, three oscicles in the middle ear, a muscular diaphragm separating the thoracic and abdominal cavities, red blood cells without nuclei, and embryonic development in the allantois and amnion.

The term "reptile", as used herein, is defined as any member of the class Reptilia which is a class of terrestrial vertebrates which characteristically lack hair, feathers, and mammary glands, their skin being covered with scales, they have a three chambered heart, and their pleural and peritoneal cavities are continuous.

A heterologous protein, as used herein, is defined as a protein comprised of inhibin protein, or a fragment thereof, and a carrier protein. It is to be understood that the terms "inhibin" and "fragment of inhibin" are used interchangeably in the heterologous protein composition, the method of making the heterologous protein, and the method of using the heterologous protein of the present invention.

It is also to be understood that "cINA$_{521}$", as used herein, denotes a 521 base pair sequence (SEQ ID NO:1). cINA$_{521}$ codes for a portion of the alpha-inhibin subunit of an chicken, represented by SEQ ID NO:2. As used herein, "MBP-cINA$_{521}$" is the heterologous protein that is expressed from a recombinant host cell, after cloning cINA$_{521}$ into a recombinant host cell and expressing a fused heterologous protein comprising maltose binding protein ("MBP") and the inhibin protein alpha-subunit fragment encoded by cINA$_{521}$. Preferably, MBP-cINA$_{521}$ is produced in host E. coli cells after expression of cloned cINA$_{521}$ using the commercially available vector pMAL™-c. Accordingly, "cINA$_{521}$" denotes a nucleotide sequence, and "MBP-cINA$_{521}$" denotes a fused heterologous protein.

A fused heterologous protein, as used herein, is defined as two different proteins fused together. For example, a protein comprised of inhibin protein, or a fragment thereof, fused to a carrier protein. The fused heterologous protein is expressed from an expression system comprising a fused gene product which contains a gene encoded for the expression of inhibin protein, or a fragment thereof, fused to a gene encoded for expression of a carrier protein. "Fused gene product", as used herein, is defined as the product resulting from the fusion of the gene encoded for the expression of inhibin protein, or a fragment thereof, and the gene encoded for the expression of a carrier protein.

A conjugated heterologous protein, as used herein, is defined as a protein comprised of inhibin protein, or a fragment thereof, conjugated to a carrier protein. The conjugated heterologous protein is produced by a chemical reaction which links the inhibin protein to the carrier protein with a covalent bond.

An immunological response of an animal to a substance which has been administered to the animal, as used herein, is defined as the cell-mediated and/or humoral response of an animal which is specifically directed against the substance.

The term "selectively interact", as used herein, is defined as where two objects associate with each other by a covalent bond, a noncovalent bond, a hydrogen bond, electrostatically, a receptor-ligand interaction, a enzyme-substrate interaction, or by other binding or attachment means. The association is selective in that the two objects interact in a specific manner, in a specific position, or only with each other.

Inhibin Compositions

The present invention relates in general to a composition used in a method of enhancing production performance in animals, including birds. The composition is comprised of a heterologous protein comprising inhibin protein, or a fragment thereof, and a carrier protein. The inhibin can be inhibin from any species of animal that produces inhibin. The inhibin includes, but is not limited to, bird inhibin, mammal inhibin, reptile inhibin, amphibian inhibin, or fish inhibin, among others. More specifically, the mammal inhibin includes, but is not limited to, cow inhibin, human inhibin, horse inhibin, cat inhibin, dog inhibin, rabbit inhibin, sheep inhibin, mink inhibin, fox inhibin, otter inhibin, ferret inhibin, raccoon inhibin, donkey inhibin, rat inhibin, mouse inhibin, hamster inhibin, and pig inhibin. The bird inhibin includes, but is not limited to, ostrich inhibin, emu inhibin, rhea inhibin, cassowary inhibin, kiwi inhibin, turkey inhibin, quail inhibin, chicken inhibin, duck inhibin, goose inhibin, and inhibin from members of the order psittaciformes.

A preferred inhibin is avian, or bird, inhibin. A more preferred inhibin is ratite inhibin, such as ostrich, emu, or rhea inhibin. An especially preferred inhibin is ostrich inhibin. Another preferred inhibin is chicken inhibin. Most preferably, the heterologous protein of the present invention comprises alpha-subunit inhibin protein, or a fragment thereof, and a carrier protein.

The inhibin, or fragment thereof, can be isolated from animal fluids, expressed from genetically engineered cells in an expression system, or synthetically produced from a series of chemical reactions. More particularly, the fragment of inhibin includes, but is not limited to the following compositions: α-subunit inhibin; β-subunit inhibin; recombinant DNA derived fragments of α-subunit inhibin or β-subunit inhibin; synthetic peptide replicas of fragments of α-subunit inhibin or β-subunit inhibin; synthetic peptide replicas of the N-terminal sequence of α-subunit inhibin or β-subunit inhibin; fragments of partially purified inhibin from follicular fluid; fragments of endogenous α-subunit inhibin or β-subunit inhibin; and fragments of exogenous α-subunit inhibin or β-subunit inhibin. As stated above, it is most preferable that the fragment of inhibin is alpha (α)-subunit inhibin, or a fragment thereof. By inhibin, it is understood by one of ordinary skill in the art to encompass inhibin with amino acid substitutions that might render it more immunogenic, or more active at a receptor.

The inhibin in the heterologous protein is either fused to or conjugated with the carrier protein as described below. Where the inhibin is fused to the carrier protein, the heterologous protein is a "fused heterologous protein". Where the inhibin is conjugated to the carrier protein, the heterologous protein is a "conjugated heterologous protein". A preferred heterologous protein is a fused heterologous protein.

The identity of the carrier protein in the heterologous protein is not a critical aspect of the present invention. Any carrier protein known in the art can be used in the heterologous protein. The carrier proteins that can be used in the present invention include, but are not limited to the following group: maltose binding protein "MBP"; bovine serum albumin "BSA"; keyhole limpet hemocyanin "KLH"; ovalbumin; flagellin; thyroglobulin; serum albumin of any species; gamma globulin of any species; syngeneic cells; syngeneic cells bearing Ia antigens; and polymers of D- and/or L- amino acids. A preferred carrier protein is MBP. Another preferred carrier protein is BSA if the heterologous protein will not be administered to a cow or horse. Yet another preferred carrier protein is ovalbumin if the heterologous protein will not be administered to a bird. The most preferred carrier protein is MBP. It is preferred that the carrier protein is immunogenic to the animal that it will be administered to.

The present invention also relates to a method of producing the conjugated heterologous protein of the present invention. Methods of producing conjugated proteins are well known in the art. Methods of conjugating proteins to proteins are fully described in Antibodies, A Laboratory Manual, edited by Ed Harlow & David Lane, Coldspring Harbor Lab (1988), which is incorporated herein by reference. Additional methods of producing conjugated heterologous proteins, including conjugation reagents, such as dialdehydes, carbodiimides, bisdiazotized benzidine and others, carrier proteins, and immunization schedules are described in detail in Chapter 38, pp. 605–618 and Chapter 42, pp. 665–678, in Section VI, "Preparation of Antibodies" in Neuroendocrine Peptide Methodology, edited by P. Michael Conn, Academic Press, New York, 1989, which is incorporated herein by reference.

Although conjugated proteins may be used in the methods of the present invention, fusion proteins are preferred. More particularly, heterologous proteins that are fused yield a homogeneous product, wherein the different segments of the proteins are always fused in the same position, and the same amount of the segments of the proteins are fused. Also, fused heterologous proteins can be produced uniformly, inexpensively, and in large quantities. In contrast, conjugated heterologous proteins are not as uniform as fused proteins. For example, depending on what proteins are being conjugated, the conjugation reaction may yield a mixture of proteins having one or more conjugations, proteins having conjugations in different locations, or proteins that remain unconjugated. Further, some of the conjugations may render the heterologous protein sterically hindered for its intended use (e.g., the immunogenic portion of the protein is sterically hindered). Also, conjugation reaction conditions and reagents may degrade the proteins produced therein. For example, glutaraldehyde is commonly used in conjugation reactions, and it modifies the conformation of proteins. Further, conjugated proteins are more expensive to produce in large quantities than fused proteins.

The present invention is also directed to a fusion gene product comprising a gene encoded for the expression of alpha-subunit inhibin protein, or a fragment thereof, and a gene encoded for the expression of a carrier protein. The gene encoded for the expression of inhibin protein, or fragment thereof, may be encoded to express avian inhibin, mammalian inhibin, fish inhibin, or reptilian inhibin. The gene encoded for the expression of a carrier protein may be encoded to express maltose binding protein or bovine serum albumin, among others. The preferred gene encoded to express a carrier protein is encoded to express maltose binding protein. The fusion gene product and the method of making the fusion gene product are described more fully below.

Briefly described, the method of producing the fused heterologous protein of the present invention is comprised of the steps of inserting a fusion gene product into a coding region of a plasmid, transformation into a host cell with the plasmid, and expressing the fused heterologous protein from the host cell by methods well known in the art. More particularly, the method of producing the fused heterologous protein comprises inserting cDNA which is encoded for expressing inhibin, or a fragment thereof, into a vector which contains coding information for the production of a carrier protein. After inserting the vector into an expression system, the fused heterologous protein is expressed by the system.

Many methods of making fused heterologous proteins are known in the art. Therefore, any method known in the art can be used to produce the fused heterologous protein of the present invention. Many commercially available vector kits and expression systems can be used to prepare the fused heterologous protein of the present invention. An example of such a commercially available vector kit and expression system is pMAL™-c of New England Biolabs, Beverly Massachusetts. Cytoplasmic expression of the fused heterologous protein occurs in the pMAL™-c system. The method of producing the fused heterologous protein of the present invention from a pMAL™-c kit is fully described below in Examples 1 and 2. Other sources of vector kits and expression systems which can be used to produce the fused heterologous protein of the present invention include, but are not limited to: Pharmacia Biotech of Piscataway, N.J.; and Clonetech, of Palo Alto, Calif.

The present invention further relates to a fusion gene product comprising a gene encoded for the expression of inhibin protein, or a fragment thereof, and a gene encoded for the expression of a carrier protein. The inhibin gene can be from any species of animal that produces inhibin. The inhibin gene can be a bird inhibin gene, a mammal inhibin gene, a reptile inhibin gene, an amphibian gene, or a fish gene, among others. More specifically, the mammal inhibin gene includes, but is not limited to, bovine inhibin gene, human inhibin gene, equine inhibin gene, cat inhibin gene, dog inhibin gene, sheep inhibin gene, mink inhibin gene, fox inhibin gene, otter inhibin gene, ferret inhibin gene, raccoon inhibin gene, rat inhibin gene, mouse inhibin gene, hamster inhibin gene, donkey inhibin gene, and pig inhibin gene. The bird inhibin gene includes, but is not limited to, an ostrich inhibin gene, an emu inhibin gene, a rhea gene, a cassowary inhibin gene, a kiwi inhibin gene, a turkey inhibin gene, a quail inhibin gene, a chicken inhibin gene, an inhibin gene from any member of the order psittaciformes, an inhibin gene from any falconiformes, an inhibin gene from any piciformes, an inhibin gene from any strigiformes, an inhibin gene from any coraciformes, an inhibin gene from any ralliformes, an inhibin gene from any passeriformes, an inhibin gene from any cuculiformes, an inhibin gene from any columbiformes, an inhibin gene from any galliformes (domestic fowl), an inhibin gene from any anseriformes (geese, ducks, other water fowl), an inhibin gene from any herodiones, and an inhibin gene from any of the following birds: falcon, eagle, hawk, pigeon, parakeet, cockatoo, makaw, parrot, canary, mynah, toucan, and perching bird (such as, song bird, jay, blackbird, finch, warbler, and sparrow).

A preferred inhibin gene is a bird inhibin gene. A more preferred inhibin gene is a ratite inhibin gene. An especially preferred inhibin gene is an ostrich inhibin gene. Another preferred inhibin gene is an emu inhibin gene. Yet another preferred inhibin gene is a rhea inhibin gene. Another preferred inhibin gene is a chicken inhibin gene.

The chicken inhibin α-subunit cDNA clone (cINA6; Wang and Johnson, Complementary Deoxyribonucleic Acid Cloning and Sequence Analysis of the α-Subunit of Inhibin from Chicken Ovarian Granulosa Cells, *Biology Of Reproduction*, 49: 453–458, 1993), which is hereby incorporated by reference in its entirety, inserted into the EcoR 1 site of Bluescript (Stratagene, La Jolla, Calif.), was obtained as a gift from P. A. Johnson (Cornell University). The cINA6 clone specifically hybridized to ostrich genomic DNA in Southern assays indicating significant DNA homology between these two species (Chouljenko et al., Expression and purification of chicken α-inhibin as a fusion protein with the *E. coli* matlose binding protein, *Poultry Science*, 73(Suppl. 1): 84, 1994). A DNA fragment ("cINA$_{521}$") was excised from the cINA6 clone using Pst I digestion. The cINA$_{521}$ DNA fragment encompassed most of the mature chicken inhibin α-subunit. Although cINA$_{521}$ was excised from the cINA6 clone reported in Wang and Johnson, the sequence obtained, namely SEQ ID NO:1, differs from the DNA sequence published in Wang and Johnson.

The ostrich inhibin α-subunit sequence was obtained by polymerase chain reaction (PCR) methods that are well known in the art. More particularly, the primers were constructed based on the sequence reported in Wang, and were used in a PCR reaction with ostrich genomic DNA: 5'-CTCAGCCTGCTGCAGCGCCC-3'(SEQ ID NO:3); and 5'-GTGTCGACCGCGCGACGCCGAC-3'(SEQ ID NO:4). More particularly, the above primers correspond to base pairs 778 to 798 and 1347 to 1326, respectively, of the chicken inhibin α-subunit cDNA clone, cINA6, reported in Wang and Johnson. The PCR-product was digested with Pst1 endonuclease and subcloned into commercially available vector PUC19 (New England Biolabs). The sequence of the ostrich Pst1 fragment inhibin gene is identical to the corresponding portion of the chicken alpha inhibin.

As stated above, it is to be understood that the carrier protein is not a critical aspect of the present invention. Therefore, a gene encoded to express any carrier protein can be used in the present invention. The carrier protein gene includes, but is not limited to, genes encoded for expressing the following proteins: maltose binding protein "MBP"; bovine serum albumin "BSA"; keyhole lympet hemocyanin "KLH"; ovalbumin; flagellin; thyroglobulin; serum albumin of any species; gamma globulin of any species; and polymers of D- and/or L- amino acids. A preferred carrier protein gene is a gene encoded to express MBP. Another preferred carrier protein gene is a BSA gene if the resultant heterologous protein will not be administered to a cow or horse. Yet another preferred carrier protein gene is an ovalbumin gene if the resultant heterologous protein will not be administered to a bird. The most preferred carrier protein gene is a gene encoded to express MBP or derivatives thereof. The preferred carrier protein genes code for proteins that will increase both the intensity and duration of the host's immune response to the inhibin protein.

The present invention further relates to a method for making a fusion gene product comprising the step of fusing a gene encoded for the expression of inhibin protein, or a fragment thereof, to a gene encoded for the expression of a carrier protein. Briefly described, the method of making the fusion gene of the present invention comprises the steps of isolating the desired inhibin complementary DNA (cDNA), producing double strand inhibin DNA, obtaining double strand carrier protein DNA, and fusing the double strand inhibin DNA to the double strand carrier protein DNA in a manner such that the fused DNA enables the expression of a fused heterologous protein comprising the inhibin protein, or a fragment thereof, and the carrier protein.

Many methods of isolating genes and making fusion gene products are known in the art. See, for example, Sambrook, Fritsch & Maniatis, Molecular Cloning, A Laboratory Manual, 2nd Ed., Cold Spring Harbor Laboratory Press, 1989, Vols. I, II, III. Therefore, any method known in the art can be used to produce the fusion gene product of the present invention. Many commercially available vector kits can be used to prepare the fusion gene product of the present invention. An example of such a commercially available vector kit is pMAL™-c of New England Biolabs, Beverly, Mass. The method of producing the fusion gene product of the present invention from a pMAL™-c kit is fully described below in Example 1. Other sources of vector kits which can be used to produce the fused gene product of the present invention include, but are not limited to: Pharmacia Biotech of Piscataway, N.J.; and Clonetech, of Palo Alto, Calif.

As stated above, the chicken inhibin α-subunit cDNA clone (cINA6) inserted into the EcoR 1 site of Bluescript was obtained as a gift of P. A. Johnson (Cornell University). A DNA fragment ("cINA$_{521}$") was excised from the cINA6 clone using Pst I digestion. This fragment (cINA$_{521}$) was cloned in plasmid p-MAL™-c in frame with the maltose binding protein ("MBP") and a fusion protein of appropriate size (Lane E; FIG. 1) was detected after IPTG (isopropyl β-D-thiogalactopyranoside) induction and SDS-PAGE. The resulting protein conjugate ("MBP-cINA$_{521}$") was used as an antigen to immunize pre-pubescent, female Japanese quail (Coturnix coturnix japonica) against circulating inhibin levels as is fully described in Example 8.

Methods of Enhancing Production Performance

It has been unexpectedly discovered that the composition of the present invention enhances the production performance of animals, and in particular the production performance of birds. Accordingly, the present invention is also directed to a method of enhancing production performance in animals via the administration of the heterologous protein of the present invention. In one embodiment, the method comprises administering an effective amount of the protein to a female animal such that production performance of the animal is increased. In another embodiment, the method comprises administering an effective mount of the protein to a male animal such that production performance of the animal is increased. Preferably, an immunological response occurs in the animal directed against the protein. More preferably, the immunological response which occurs in the animal is also directed against the inhibin protein produced by the animal (endogenous inhibin).

More particularly, the method of the present invention comprises the administration of an effective mount of the heterologous protein of the present invention (comprising inhibin, or a fragment thereof, and a carrier protein) to an animal such that the production performance of the animal is enhanced. Preferably, the animal is a bird. It is to be understood that a "treated" bird is a bird to which the heterologous protein of the present invention has been administered.

The method of the present invention can be used to enhance production performance in any species of female bird that produces inhibin. The female bird includes, but is not limited to, a ratite, a psittaciformes, a falconiformes a piciformes, a strigiformes, a passeriformes, a coraciformes, a ralliformes, a cuculiformes, a columbiformes, a galliformes (domestic fowl), an anseriformes (geese, ducks, other water fowl), and a herodiones. More particularly, the female bird includes, but is not limited to, an ostrich, emu, rhea, kiwi, cassowary, turkey, quail, chicken, falcon, eagle, hawk, pigeon, parakeet, cockatoo, makaw, parrot, perching bird (such as, song bird, jay, blackbird, finch, warbler, sparrow), and any member of the order psittaciformes. A preferred bird is a ratite. A more preferred bird is an ostrich. Another preferred ratite is an emu. Yet another preferred ratite is a rhea. Another preferred bird is any member of the order psittaciformes. Yet another preferred bird is a chicken. Still another preferred bird is a quail. The method of the present invention can also be used to accelerate the onset of egg lay in species of birds that are endangered. Such endangered birds include, but are not limited to, eagles, hawks, condors, and owls.

The inhibin and the carrier protein in the heterologous protein composition of the present invention vary according to what species of bird the composition will be administered to. It is preferred that avian inhibin and maltose binding protein is used when the composition is to be administered to a bird. A preferred inhibin is domestic chicken or ratite inhibin when the composition is to be administered to a ratite. More preferably, the preferred inhibin is domestic chicken or ostrich inhibin when the composition is to be administered to an ostrich or ratite. Another preferred inhibin is domestic chicken or ostrich inhibin when the composition is to be administered to a chicken. It is to be understood that the inhibin in the heterologous protein need not be from the same species to which the heterologous protein will be administered. For example, a heterologous protein that is administered to an ostrich can be comprised of chicken inhibin and a carrier protein.

It is also to be understood that the composition can further comprise adjuvants, preservatives, diluents, emulsifiers, stabilizers, and other known components that are known and used in vaccines of the prior art. Any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), Titermax® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate. A preferred adjuvant system is Freund's incomplete adjuvant. Another preferred adjuvant system is Freund's complete adjuvant.

The heterologous protein composition of the present invention can be administered to a bird by any means known in the art. For example, the composition can be administered subcutaneously, intraperitonealy, intradermally, or intramuscularly. Preferably, the composition is injected subcutaneously. The composition can be administered to the bird in one or more doses. Preferably, the composition is administered to the bird in multiple doses wherein an initial immunization is followed by booster immunizations.

The composition can be administered to an animal at any time before the animal ceases to ovulate or produce sperm due to disease or age. The preferred age at which the composition of the present invention is administered to an animal depends upon the species of the animal involved, the mating season (if any) of an animal, and upon the purpose of the administration of the composition.

For example, where the composition is administered to accelerate the onset of egg lay or sperm production, the composition of the present invention is to be administered to a bird before the bird reaches egg lay or puberty. As stated above, the preferred age at which the composition of the present invention is first administered to an animal depends upon the species of the animal involved, the mating season (if any) of an animal, upon the size of the bird, and upon the identity of the components (inhibin and carrier protein) in the composition.

As another example, where the composition is administered to enhance production performance of agricultural animals which have breeding seasons, the preferred time of administering the composition is prior to the start of the breeding season. In contrast, where the composition is to be administered to a mature animal which has a suppressed egg production rate or a suppressed sperm production rate, then the composition would be administered at the time that the suppression is recognized as problematic.

With respect to an animal having a breeding season, although the heterologous protein of the present invention can be administered to a bird such as a ratite at any age, immunizing the bird during the six months prior to the bird's first breeding season is preferable. It is understood by those of ordinary skill in the art that average female birds initiate egg lay during the first breeding season. It is even more preferable to immunize the bird approximately six months prior to the bird's first breeding season, and then to administer booster immunizations at one month intervals prior to the bird's first breeding season. It is most preferable to immunize the bird approximately six months prior to the bird's first breeding season, and then to administer booster immunizations at one month intervals for six months.

For example, for best results in increasing the egg production of a female ostrich, a primary immunization is administered to the ostrich approximately 6 months before its first breeding season, and then booster immunizations are administered at one month intervals for six months. The primary immunization comprises between approximately 0.5 to 4.5 mg of the heterologous protein of the present invention. The booster immunizations comprise between approximately 0.30 to 3.0 mg of the heterologous protein of the present invention. Preferably, the primary immunization comprises between approximately 1.5 to 3.0 mg of the heterologous protein of the present invention. The booster immunizations comprise between approximately 0.75 to 1.5 mg of the heterologous protein of the present invention. It is also preferable that the heterologous protein is emulsified in Freund's Complete Adjuvant (Sigma Chemical Co., St. Louis, Mo.) in the primary immunization, and that the heterologous protein is emulsified in Freud's Incomplete Adjuvant (Sigma) in the booster immunizations. Even more preferably, the heterologous protein composition is injected subcutaneously. Most preferably, the heterologous protein composition is injected subcutaneously at three sites along the upper thigh region of the ostrich.

The amount administered to a bird of the heterologous protein of the present invention varies according to the species of the bird, the age and weight of the bird, when the protein is administered in relation to the breeding season (if the bird has a breeding season), and how many times the protein is to be administered. Also, the commencement of the administration schedule, or treatment schedule, varies according to the species of the bird, the average age of puberty of that species of the bird, the family history of the bird (with respect to the family's history of age at puberty), the time of year the bird was hatched, the nutritional plane of the bird (highly fed birds come into puberty before those that are undernourished), the general health of the bird at that time of commencement, immunological competence of the bird, the long term health history of the bird, the presence of extreme weather conditions (prolonged excessive inclement weather such as rain, heat, or windiness that the bird is not accustomed to), housing conditions (overcrowding), and a lack of exercise.

One of ordinary skill in the art, in view of the teachings of the present invention, would be able to determine by routine testing the amount of heterologous protein that will be necessary to elicit an immunological response to the protein by the bird.

Another example of the method for enhancing production performance is as follows. An immunologically effective amount of a conjugated heterologous protein composition is administered to a mammal such that an immunological response occurs in the mammal which is directed against the heterologous protein. The heterologous protein is preferably comprised of mammalian inhibin conjugated to maltose binding protein. Another preferred conjugated heterologous protein is comprised of arian or reptilian inhibin, and maltose binding protein.

For example, the following is a brief summary of the method of the present invention for enhancing production performance in Japanese Quail as is fully discussed in Example 8. The average age at puberty for an untreated quail is approximately six to eight weeks. The following would be the treatment schedule for Japanese quail having an approximate body weight range of 0.1 to 0.25 pounds: primary (first) injection of 0.75 mg of the heterologous protein of the present invention on its 25th day of age; and boosters of 0.375 mg on the 32nd, 39th, 46th, 53rd, 60th, and 90th day of age, followed by boosters every 35 days thereafter for three additional challenges (i.e., at 95, 130, and 165 days-of-age.).

More particularly, at 25 days-of-age, 50 female quail were randomly and equally assigned to one of two injection groups (25 birds per group) as follows: (1) MBP-cINA$_{521}$ in Freund's adjuvant ("MBP-cINA$_{521}$/FRN"), or (2) Freund's (adjuvant control; "FRN"). Birds immunized against inhibin (Group 1) were given approximately 0.75 mg MBP-cINA$_{521}$ per bird in the appropriate control vehicle. Equivalent vehicular injection volumes (0.2 mL) of FRN were used in Group 2. All injections were given subcutaneously using tuberculin syringes fitted with 25 gauge needles. As discussed above, booster inhibin immunizations of approximately 0.375 mg MBP-cINA$_{521}$ per bird, or appropriate control challenges, were subsequently administered and the birds were observed for a total of 20 weeks Beginning at 41 days-of age, which is considered to be day 1 of the egg lay cycle, daily hen-day egg production ("HDEP") and mortality ("MORT") measures were recorded for 20 consecutive weeks. In addition, average age at first egg lay ("FIRST") and age at which hens reached 50% egg production ("FIFTY") were calculated for each of the treatment groups. As is more fully discussed in Example 8, HDEP, MORT, FIRST, and FIFTY data were subjected to analyses of variance.

Inhibin immunoneutralization clearly accelerated puberty in the quail hens. As shown in Table 2, the average age of FIRST egg lay was decreased (P<0.0088) by nearly six days in inhibin-treated hens. Likewise, as shown in Table 3, the age to FIFTY egg production was markedly reduced (12 days; P<0.01) in inhibin-treated hens.

Figure 2:
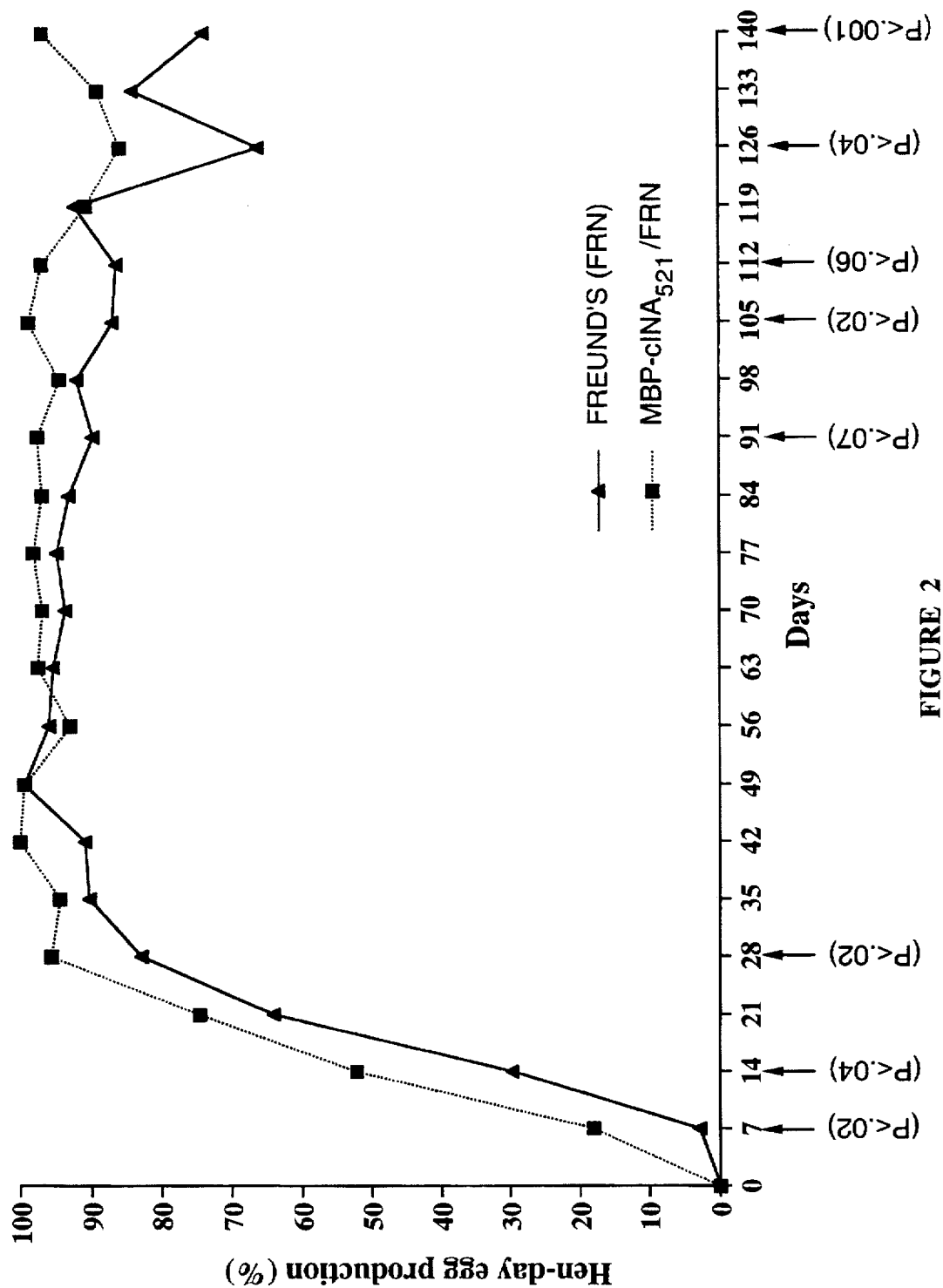
FIG. 2 is an illustration of the effect of inhibin α-subunit immunoneutralization on hen-day egg production ("HDEP") in Japanese Quail using maltose binding protein fused with the protein encoded by $cDNA_{521}$. More particularly.

A positive effect of inhibin treatment on intensity of egg lay was also extant, most notably at the beginning and at the end of the laying cycle, as shown in FIG. 2. For example, significantly greater (P<0.05) mean HDEP rates were observed in hens treated with MBP-cINA$_{521}$/FRN when compared to the FRN controls during Weeks 1 (16.5 vs 2.6%), 2 (50.0 vs 28.6%), and 4 (96.6 vs 79.7%) and again during Weeks 15 (98.8 vs 86.9%), 16 (96.9 vs 86.3%), 18 (85.7 vs 66.1%), and 20 (96.8% vs 73.8%). Total HDEP rate, inclusive of all 20 weeks of lay, for inhibin-treated hens was 83.5% as compared to 75.4% for the controls (P<0.14).

Besides accelerating puberty, prolonging egg lay, and enhancing the overall intensity of lay, inhibin-treatment decreased the time needed to reach peak egg lay by approximately 3 weeks. Referring now to FIG. 2, compare MBP-cINA$_{521}$/FRN which is at 96.6% HDEP by Week 4 versus FRN which is at 96.6% HDEP by Week 7. Although differences in peak HDEP values were not statistically evaluated, the treatment differences in mean age at which hens reached 50% HDEP levels (FIFTY) reflect peak performance.

Mortality was not a factor in this study as only eight birds have died (three controls, five treated). The mortality of 16% is within expected limits for quail that have reached 180 days-of-age.

Most timed biological responses to treatments are studied for effects on onset, magnitude, and duration of response. Herein, the data represent what most would consider to be a full cycle of lay in Japanese quail (i.e., 20 weeks post-initiation of puberty or egg lay). Therefore, the following comments on the effects of inhibin immunoneutralization on the onset, magnitude and duration of egg lay in this species are justified.

The data support the conclusion that onset of puberty was accelerated in the inhibin immunoneutralized group. This was evidenced in the marked treatment differences noted in both the FIRST and FIFTY variables and in the differences observed during the initial weeks of HDEP data.

The acceleration of puberty coupled with the increased persistency of egg lay in the inhibin-challenged birds contributed to an increase in overall HDEP that was marked (8.1%). For example, on a per-hen basis, inhibin treatment essentially translated into a daily gain of approximately 0.081 eggs for every day of the laying cycle that a hen remained viable (i.e., capable of laying an egg). This means that approximately 11 more eggs were obtained for each hen housed during the 20 week period examined (0.081 eggs/hen×140 days-of-lay=11.34 eggs per hen per laying cycle).

Similar results in chickens and turkeys, as found in Coturnix, will have substantial strategic relevance to the poultry industry. It should be noted that Japanese quail have been selected for intensity of egg lay, and that egg laying potential is considered to be even greater in Cornmix than in chicken hens (Single Comb White Leghorns) commercially reared for the single purpose of production of table eggs. Therefore, intensification of egg lay by inhibin vaccination in chickens which have not been selected for egg production but for meat production, e.g., broiler breeders raised for the consumption of their flesh, may be even greater.

Accordingly, the above data shows that the inhibin composition of the present invention enhances production performance as it accelerates the onset of puberty, increases egg lay intensity, and accelerates the onset of maximum egg lay in Japanese Quail. Since Japanese Quail are an acceptable animal model for chickens with respect to their reproductive systems, the above data indicates that the method of the present invention will also accelerate the onset of egg lay in chickens. Accordingly, the method of the present invention will result in an egg producer being able to produce more eggs with lower feed costs.

The above data also shows that the inhibin composition of the present invention enhanced production performance as it minimized the adverse affects of elevated temperatures of the egg lay rate of the Japanese Quail. More particularly, in the eighteenth week of the study described in Example 8, the Quail were inadvertently exposed to elevated temperatures. As can be seen in FIG. 2, the birds in Group 1 (treated with MBP-cINA$_{521}$/FRN) sustained a drop in egg lay rate of approximately 5%. In contrast, the birds in Group 2 (control: FRN) sustained a drop in egg lay rate of approximately 26%. Accordingly, the method of the present invention of enhancing production performance ameliorates the negative impact on egg lay rates of poultry exposed to adverse egg laying conditions. This aspect of the present invention is significant as poultry are often raised in open, uncontrolled environments. Accordingly, poultry stocks are often exposed to adverse conditions such as elevated temperatures, and other extreme weather conditions that they are not acclimated to, which thereby decrease egg lay rates in the poultry industry.

The following is a brief summary of the method of the present invention for enhancing production performance in ostriches as is discussed in Example 9. The average age at puberty for untreated ostriches is between approximately 28 and 32 months. The following would be the treatment schedule for ostriches having an approximate body weight range of 150 to 300 pounds: primary (first) injection of 5.0 mg of the heterologous protein of the present invention on its 26th month of age; and boosters of 2.5 mg on the 27th, 28th, 30th, 32nd, 34th, and 36th month of age.

The following is a brief summary of the method of the present invention for enhancing production performance in emu as is discussed in Example 10. The average age at puberty for untreated emu is approximately 20 months. The following would be the treatment schedule for emu having an approximate body weight range of 50 to 90 pounds: primary (first) injection of 3.0 mg of the heterologous protein of the present invention on its 18th month of age; and boosters of 1.5 mg on the 19th, 20th, 22nd, 24th, 26th, and 30th month of age.

The following is a brief summary of the method of the present invention for enhancing production performance in chickens as is discussed in Example 11. The average age at puberty for an untreated chicken is approximately 20 weeks. The following would be the treatment schedule for a chicken having an approximate body weight range of 2.0 to 3.5 pounds: primary (first) injection of 1.5 mg of the heterologous protein of the present invention on its 15th week of age; and boosters of 0.75 mg on the 17th, 20th, 24th, 30th, 40th, and 50th week of age.

The following is a brief summary of the method of the present invention for enhancing production performance in turkeys as is discussed in Example 12. The average age at puberty for an untreated turkey is approximately 30 weeks. The following would be the treatment schedule for a turkey having an approximate body weight range of 9.0 to 12 pounds: primary (first) injection of 2.0 mg of the heterologous protein of the present invention on its 28th week of age; and boosters of 1.0 mg on the 29th, 30th, 34th, 38th, 46th, and 54th week of age.

The following is a brief summary of the method of the present invention for enhancing production performance in parrots as is discussed in Example 13. The average age at puberty for an untreated parrot is approximately 30 months. The following would be the treatment schedule for a parrot having an approximate body weight range of 0.5 to 1.25 pounds: primary (first) injection of 0.75 mg of the heterologous protein of the present invention on its 28th month of age; and boosters of 0.375 mg on the 29th, 30th, 32nd, 34th, 36th, and 38th month of age.

As discussed above, the method of the present invention enhanced production performance by accelerating the onset of puberty in the animal that the composition of the present invention was administered to. The term "accelerates" with respect to the onset of egg lay denotes that egg lay of a treated bird commences at least about 3% earlier than egg lay would ordinarily commence in an untreated bird. Preferably, egg lay commences at least about 5% earlier, and more preferably commences at least about 7% earlier. Even more preferably, egg lay commences at least about 10% earlier, and most preferably commences at least about 13% earlier than egg lay would ordinarily commence in an untreated bird.

Also, as discussed above, the method of the present invention enhanced production performance by increasing egg or sperm production intensity in animals. The term "increases" with respect to egg production denotes that egg production of a treated bird increases at least about 3% with respect to the amount of egg production in an untreated bird. Preferably, egg production increases at least about 7%, and more preferably increases at least about 12%.

Further, as discussed above, the method of the present invention enhances production performance by accelerating the onset of maximum egg production in an animal. The term "accelerates" with respect to the onset of maximum egg lay denotes that maximum egg lay of a treated bird commences at least about 3% earlier than egg lay would ordinarily commence in an untreated bird. Preferably, maximum egg lay commences at least about 5% earlier, and more preferably commences at least about 7% earlier. Even more preferably, maximum egg lay commences at least about 10% earlier, and most preferably commences at least about 13% earlier than maximum egg lay would ordinarily commence in an untreated bird.

Surprisingly, the composition of the present invention can also be used to increase the lifetime total egg lay of birds. The term "increase" with respect to total lifetime egg lay denotes that the total lifetime egg lay of a treated bird increases at least about 3% with respect to the total lifetime egg lay of an untreated bird. Preferably, total lifetime egg lay increases at least about 7%, and more preferably increases at least about 12%. Most preferably, total lifetime egg lay increases at least about 15%.

Unexpectedly, the composition of the present invention can also be used to decrease or eliminate the need to molt a female bird, e.g., to prolong egg laying persistency by providing for a second cycle of lay. More particularly, if the composition described above is continually administered to the female bird, as disclosed in the method above, the rate of egg lay of the bird, in comparison to if the bird was not treated with the composition of the present invention, would remain high enough so that the bird would not need to be melted to improve its rate of egg lay. It is a common practice in the art to molt a female bird, such as chicken hens (Single Comb White Leghorns, table egg producers), when its egg lay production declines such that the economic cost of maintaining the bird outweighs the economic benefit yielded by the eggs produced. To "molt" a chicken hen, the bird undergoes a period of fasting of approximately four to fourteen days until it beings to molt, e.g., lose its feathers. During the molting period, the bird stops laying eggs. After the bird is placed back onto normal levels of feed, egg production recommences after a period of time. The entire molting period is approximately two months from the beginning of the fast period to the onset of the next egg-lay cycle. In effect, the egg production rate of the bird is rejuvenated. However, after molting a chicken, its rate of egg-lay in the next cycle does not equal the egg production during the first (pre-molt) egg-lay cycle. M. North and D. Bell, Commercial Chicken Production Manual, fourth edition, Chapter 19, Published by Van Norstrand Reinhold of New York.

For example, chickens reach egg lay at approximately 20 weeks, and produce an economically significant number of eggs for approximately 40 to 50 weeks. At the peak of egg lay, chickens produce eight to nine eggs every ten days. However, after approximately 50 weeks of egg lay, the rate of egg production decreases to approximately 60% of peak egg lay. At this point, the cost of the feed for the chicken is greater than the value of the eggs its produces. It is common practice to molt the chicken at this point, so that when the chicken recommences egg lay, its rate of egg lay is increased. By "prolonging the persistence of egg lay" with reference to chickens and quail, among other birds, it is meant that egg lay will be prolonged for approximately one to four weeks.

Therefore, the composition of the present invention, as it maintains the rate of egg lay at a higher level than if the bird were not treated with the composition, reduces or eliminates the need to molt a bird. The reduction or elimination of the need to molt a bird results in significant savings. More particularly, during the period that a bird is molted, and prior to that time, the bird has been unproductive with respect to its feed cost before it is molted, and then it is unproductive for a period of time after feeding recommences. Maintaining the rate of egg lay at an enhanced level therefore eliminates or reduces these unproductive phases of the bird, thereby reducing the producer's costs and increasing the producer's profits. Maintaining the rate of egg lay at an enhanced level further enhances egg producer's profits as the rate of egg-lay after molting does not equal the rate of egg-lay in the first cycle of egg lay as discussed above.

Briefly described, the rate of egg lay of birds would be enhanced, thereby avoiding the need to molt the bird, by administering an effective amount of the heterologous protein of the present invention to induce an immunological response thereto, and thereafter administering an effective amount of the heterologous protein (boosters) to maintain a higher than normal rate of egg lay.

Accordingly, the method of the present invention enhances production performance in female animals which produce inhibin, such as mammals, reptiles, and birds such as ratites. More particularly, this method enhances production performance in female ratites such as ostriches, emus, and rhea, and in chickens. Unexpectedly, the method of the present invention increases the onset of puberty or first egg lay in animals. Also, the method of the present invention accelerates the onset of maximum egg lay in an animal. Further, the method of the present invention increases the number of eggs laid by an animal. Further still, the method of the present invention prolongs the persistence of maximum egg lay in animals. Still further, the method increases the lifetime total egg lay of an animal. In avians, the method of the present invention also improves the feed conversion ratio of the bird. Also, the method of the present invention unexpectedly reduces or eliminates the effect of adverse laying conditions on egg lay rates of animals exposed to such conditions. Such adverse conditions include elevated temperatures, overcrowding, poor nutrition, and noise.

Although not wanting to be limited by the following, it is theorized that the method of the present invention of enhancing production performance in animals provides a greater increase in egg production in species that have not been genetically selected for the trait of prolific egg laying. This is particularly true for certain avians. For example, egg-type chickens have been genetically selected for maximum production performance since the late 1920s. (See, for example, Jull, M. A, 1932, Poultry Breeding, John Wiley & Sons.) In terms of the short life span of a chicken, a great deal of selection for this trait occurred over the period of time from approximately 1928 to the present. In contrast, ratites and psittaciformes, most other exotic birds, and to a lesser extent meat-type chickens (broilers) have not been genetically selected for the trait of prolific egg laying. Also, birds that are endangered have also not been genetically selected for the trait of prolific egg laying. Accordingly, as egg-type chickens are already genetically excellent egg layers, the amount of improvement that can be seen with the method of the present invention is limited in comparison to birds that are genetically poor to medium egg layers. Therefore, a much greater amount of improvement in the production performance is seen with the method of the present invention with birds that have not been genetically selected for prolific egg laying, such as, ratites, psittaformes, other exotic birds, endangered birds, turkeys, and meat-type chickens.

The immunization of an animal with the heterologous protein of the present invention induces the animal to produce antibodies selectively directed against the heterologous protein. Preferably, the immunization also induces the animal to produce antibodies selectively directed against endogenous inhibin. The production of such antibodies by a bird reduces the time to the onset of puberty or egg lay. The production of such antibodies by the animal also enhances the animal's egg production capability or sperm production capability as the antibodies neutralize the biological activity of inhibin in the animal's blood stream.

Not wanting to be bound by the following theory, it is believed that the α-subunit of inhibin binds to FSH receptors and therefore competitively inhibits the binding of FSH with such receptor sites. Reducing the levels of inhibin that may bind with receptor sites, therefore increases the biological effect of the FSH in the animal as there is reduced competition for the FSH receptor sites. It is thought that the antibodies neutralize the inhibin by interacting with the circulating inhibin, thereby stearically interfering with the binding of the interacted inhibin to the FSH receptor sites.

Unexpectedly, the method of the present invention also improves production performance in male animals which produce inhibin, such as mammals, reptiles, and birds. More particularly, the method of the present invention increases testosterone levels in male animals. Similarly, the method of the present invention increases the onset of puberty or sperm production in male animals. Also, the method of the present invention accelerates the onset of maximum sperm production in a male animal. Further, the method of the present invention increases the intensity of sperm production (sperm count) by a male animal. Further still, the method of the present invention prolongs the persistence of maximum sperm production in animals. Also, the method of the present invention increases ejaculate volume in male animals. Further, the method improves sperm viability in animals. Still further, the method unexpectedly reduces or eliminates the effect of adverse conditions on sperm production of animals exposed to such conditions. Such adverse conditions include elevated temperatures, overcrowding, poor nutrition, and noise. The method of the present invention also unexpectedly increases the libido, and therefore, the reproductive potential, of a male bird.

Another unexpected and surprising aspect of the present invention is that the composition of the present invention also produces more eggs having a decreased cholesterol content in comparison to the eggs laid by untreated birds. More particularly, if the composition described above is administered to a female bird, as disclosed in the method above, the cholesterol content of the eggs laid by the bird will be reduced for a longer period of time in comparison to if the bird was not treated with the composition of the present invention. Therefore, the composition of the present invention increases or produces a greater number of low cholesterol eggs.

The terms "increase" or "greater number of" denotes that the number of low cholesterol eggs produced by a treated bird increases at least about 2% with respect to the number of low cholesterol eggs produced by an untreated bird. Preferably, the number of low cholesterol eggs produced increases at least about 5%, and more preferably increases at least about 10%. It is to be understood that a "treated" bird is a bird to which the heterologous protein of the present invention has been administered. The term "lower cholesterol" or "low cholesterol" denotes that the cholesterol content of an egg is lower than the average cholesterol content of eggs produced by that species of bird during the lifetime of such a bird by at least about 10%. Preferably, the cholesterol content of a low cholesterol egg is lower than the average by at least about 20%. More preferably, the cholesterol content of a low cholesterol egg is lower than the average by at least about 30%.

It is known that in chickens, the first five to six eggs that are laid by a female bird (hen) after it reaches puberty are lower in cholesterol than the eggs it later produces. The composition of the present invention induces the female bird to lay eggs having a lower cholesterol content for a longer period of time. Due to the health consequences linked to high cholesterol levels in the blood, there remains a need for low cholesterol egg products. Accordingly, the composition of the present invention provides the producer of eggs with a greater number of a highly sought after type of egg.

Gene Therapy using the Fusion Gene Product

The present invention also relates to a method of enhancing the production performance of animals, by administering to the animal a fusion gene product comprising a gene encoded for the expression of alpha-subunit inhibin protein, or a fragment thereof, and a gene encoded for the expression of a carrier protein. The fusion gene product of the present invention may be administered directly to the animal, or it may be administered in a vector, or in a cell containing a vector having the fusion gene product therein.

Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, and augment normal or abnormal gene function.

Strategies for gene therapy include therapeutic strategies such as identifying a defective gene and then adding a functional gene to either replace the function of the defective gene or to augment a slightly functional gene; or prophylactic strategies, such as adding a gene for the product protein. As an example of a prophylactic strategy, a fused gene product which encodes for inhibin, or a fragment thereof, and a carrier protein may be placed in an animal thereby secondarily reducing the levels of inhibin in the animal due to the immune response.

Any protocol for transfer of the fused gene product of the present invention is contemplated as part of the present invention. Transfection of promoter sequences, other than one normally found specifically associated with inhibin, or other sequences which would decrease production of inhibin protein are also envisioned as methods of gene therapy. An example of this technology is found in Transkaryotic Therapies, Inc., of Cambridge, Mass., using homologous recombination to insert a "genetic switch" that turns on an erythropoietin gene in cells. See Genetic Engineering News, Apr. 15, 1994.

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-vital vectors may be used which include liposomes coated with DNA. Such liposome/DNA complexes may be directly injected intravenously into the animal. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the animal and grown in cell culture. The DNA is transfected into the cells, the transfected cells are expanded in number and then reimplanted in the animal. In in vitro gene transfer, the transformed cells are cells growing in culture, such as tissue culture cells, and not particular cells from a particular animal. These "laboratory cells" are transfected, the transfected cells are selected and expanded for either implantation into an animal or for other uses.

In vivo gene transfer involves introducing the DNA into the cells of the animal when the cells are within the animal. Methods include using vitally mediated gene transfer using a noninfectious virus to deliver the gene in the animal or injecting naked DNA into a site in the animal and the DNA is taken up by a percentage of cells in which the gene product protein is expressed. Additionally, the other methods described herein, such as use of a "gene gun," may be used for in vitro insertion of inhibin DNA or inhibin regulatory sequences.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the animal to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms in order to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carded to the recipient cell and then resides in the cytoplasm or in the nucleoplasm. DNA can be coupled to carrier nuclear proteins in specifically engineered vesicle complexes and carried directly into the nucleus.

Gene regulation of inhibin may be accomplished by administering compounds that bind to the inhibin gene, or control regions associated with the inhibin gene, or its corresponding RNA transcript to modify the rate of transcription or translation. Additionally, cells transfected with a DNA sequence encoding inhibin, or a fragment thereof, and a carrier protein may be administered to an animal to provide an in vivo source of the heterologous protein of the present invention. For example, cells may be transfected with a vector containing the fusion gene product of the present invention, encoding inhibin, or a fragment thereof, and a carrier protein.

The term "vector" as used herein means a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising the fused gene product of the present invention is operatively linked to an expression control sequence to form an expression vector capable of expressing the heterologous protein of the present invention. The transfected cells may be cells derived from the animal's normal tissue, the animal's diseased tissue, or may be non-animal cells.

For example, cells removed from an animal can be transfected with a vector capable of expressing the heterologous protein of the present invention, and re-introduced into the animal. The transfected cells then produce the heterologous protein of the present invention thus inducing an immunological response to the inhibin. Cells may also be transfected by non-vector, or physical or chemical methods known in the art such as electroporation, ionoporation, or via a "gene gun." Additionally, the fused gene product of the present invention may be directly injected, without the aid of a carrier, into an animal. In particular, the fused gene product of the present invention may be injected into skin, muscle or blood.

The gene therapy protocol for transfecting inhibin, or a fragment thereof, into an animal may either be through integration of the fused gene product into the genome of the cells, into minichromosomes, or as a separate replicating or non-replicating DNA construct in the cytoplasm or nucleoplasm of the cell. Heterologous protein expression may continue for a long-period of time, or the fused gene product of the present invention may be reinjected periodically to maintain a desired level of the heterologous protein in the cell, the tissue, or organ, or a determined blood level.

The fused gene product of the present invention can be administered to a bird by any means known in the art. For example, the composition can be administered subcutaneously, intraperitonealy, intradermally, intravascularly, or intramuscularly. Preferably, the composition is injected subcutaneously. Another preferable administration is intravascular infusion near the preferred site of therapy. The composition can be administered to the bird in one or more doses. Preferably, the composition is administered to the bird in multiple doses wherein an initial immunization is followed by booster immunizations. The preferred amount of the fused gene product to be administered is between 50 and 300 micrograms per kilogram of body weight. Preferably, the fused gene product is administered in a carrier, such as a buffer or Freund's adjuvant.

The methods of the present invention for enhancing production performance in birds will greatly accelerate the growth of the population and therefore the market for ratites such as ostrich and emu as their suboptimal egg laying rates will be increased by the present method. The method of the present invention will also satisfy the expanding need for poultry such as domestic chickens, and their eggs.

The utility of the method of the present invention for enhancing production performance is not limited to enhancing production performance in birds. The present method for enhancing production performance can be used in many animals. As stated above, the method of the present invention is used to enhance production performance of any animal that produces inhibin, including, but not limited to, most animals that are raised agriculturally, such as pigs, cows, sheep, turkeys, quail, ducks, geese, turtles, fish, and chickens; in fur bearing animals such as mink, fox, otter, ferret, rabbits, and raccoons; rodents for laboratory testing such as mice, rats, hamsters, guinea pigs and gerbils; for animals whose hides are used for decorative purposes such as alligators and snakes; exotic or endangered species; animals used for racing, entertainment, or showing (competitions) such as horses, dogs, cats, zoo animals, and circus animals; and humans. Additional avians that the method of the present invention enhances production performance thereof include ratites, psittaciformes, falconiformes, piciformes, strigiformes, passeriformes, coraciformes, ralliformes, cuculiformes, columbiformes, galliformes, anseriformes, and herodiones. More particularly, the method of the present invention may be used to enhance production performance of an ostrich, emu, rhea, kiwi, cassowary, parrot, parakeet, makaw, falcon, eagle, hawk, pigeon, cockatoo, song bird, jay bird, blackbird, finch, warbler, canary, toucan, mynah, or sparrow.

Qualitative or Quantitative Methods of the Present Invention

Another aspect of the present invention is a method of producing antibodies directed against the heterologous protein of the present invention. Generally, the method of producing antibodies directed against the heterologous protein comprises the steps of: administering an effective amount of a heterologous protein comprising inhibin protein, or a fragment thereof, and a carrier protein, to an animal such that an immunological response occurs in the animal against the heterologous protein; removing a blood sample from the animal; and then isolating any antibodies directed against inhibin from the serum of the blood sample. Preferably, the antibodies are isolated from the serum of the blood sample by passing the serum through a column containing effective amounts of the carrier protein to separate the antibodies from the serum. Alternatively, the column will contain the heterologous protein of the present invention. In another technique, the antibodies are isolated by first passing it through a column containing the carrier protein, and then passing it through a column containing the heterologous protein of the present invention. The techniques used to produce and purify antibodies directed against the heterologous protein of the present invention are well known to one of ordinary skill in the art.

It is also to be understood that the heterologous protein of the present invention can be administered to any animal dependent upon the type of antibodies that are desired. Further, it is to be understood that the inhibin can be exogenous or endogenous. Therefore, the type of inhibin in the heterologous protein of the present invention, and the species of animal the composition is administered to is determined by what type of antibody is desired. For example, heterologous protein comprising chicken inhibin and maltose binding protein can be administered to an ostrich to produce ostrich anti-chicken inhibin antibodies. Also, heterologous protein comprising ostrich inhibin and maltose binding protein can be administered to an ostrich to produce ostrich anti-ostrich inhibin antibodies.

The present invention is also directed to a rapid, simple, reliable, cost-effective method for determining whether an animal is hormonally pre-dispositioned to be a high-level or low-level egg producer. More particularly, the present invention also relates to a method of determining the mount of inhibin produced by an animal, which therefore allows the determination of the egg production capability of the animal. Briefly described, the method of determining the quantity of inhibin in the blood of an animal, comprises the steps of: withdrawing a blood sample from an animal; contacting the blood sample with anti-inhibin antibodies that are specifically directed against the animal's endogenous inhibin under conditions which allow the antibodies to selectively interact to any inhibin if present in the sample; removing any uninteracted antibodies from any interacted antibodies; and determining the quantity of antibodies that are interacted.

One of ordinary skill in the art will understand that the immunoassay techniques that can be used in the above method are well known in the art. Therefore, any immunoassay technique, label, and visualization method known in the an can be used in the above method, including ELISA and radioimmunoassay (RIA). A preferred immunoassay is ELISA ("enzyme linked immunosorbent assay"), and a preferred label is horseradish peroxidase. Another preferred label is a colored latex bead. The colored latex bead can be any color desired for visualization purposes. Preferably, the latex bead is yellow, red, blue, or green. The colored latex bead can be hollow or solid, but it preferably is hollow to minimize its weight. The size of the latex bead varies according to its intended use in immunoassays. One of ordinary skill in the art would be able to ascertain by routine testing the largest bead size that is visible yet does not interfere stearically with the immunoassay reactions. Preferably, the latex bead is less than 0.5µ, in diameter, and most preferably it is less than 0.2µ in diameter.

For example, circulating inhibin concentrations in the blood of a bird can be determined using standard sandwich ELISA techniques. First, bind anti-inhibin antibodies which are directed against a portion of inhibin, or a fragment thereof, to the wells of a microtiter plate. After washing and blocking the plate, then add a quantity of blood plasma that was obtained from the bird to be tested. After allowing any inhibin in the sample, if present, to selectively interact with the immobilized anti-inhibin antibody, the sample is washed from the well of the plate. Next, add labeled anti-inhibin antibodies to the well that are directed against a different portion of the inhibin, or a fragment thereof, than the antibody immobilized in the well. The antibody can be labeled with any label known in the art, such as horseradish peroxidase. After allowing the labeled anti-inhibin antibody to selectively interact with any immobilized inhibin, any uninteracted labeled anti-inhibin antibodies are removed by washing. The amount of inhibin present in the plasma sample is determined by using the appropriate visualization means for the label used in the ELISA to quantify the amount of immobilized labeled anti-inhibin antibody in the well. Standard positive and negative controls are to be run simultaneously in neighboring plate wells.

It is to be understood that the reproductive potential of any animal which produces inhibin can be determined by the above method. The method of the present invention can be used to determine the amount of inhibin produced by a female animal of any species that produces inhibin. The animal can be a bird, mammal, fish, or reptile, among others. More specifically, the mammal includes, but is not limited to, a cow, human, horse, cat, dog, sheep, mink, fox, otter, ferret, raccoon, and pig. The bird includes, but is not limited to, an ostrich, emu, and chicken. A preferred animal is a bird. A more preferred animal is a ratite. An especially preferred animal is an ostrich. Another preferred animal is an emu. Yet another preferred animal is a chicken.

Animals having high levels of inhibin have low reproductive potential, and depending upon the species involved and whether they are raised for agricultural purposes, such a low egg producing animal may be taken to slaughter instead of being kept for breeding purposes. In contrast, those agriculturally raised animals having lower amounts of inhibin are higher egg producers and generally are used for breeding purposes, and are not taken to slaughter.

The inhibin level in an animal varies according to its age, species, and the time of year relative to the breeding season (if any). Therefore, the determination of the egg laying potential of an animal is relative to the these factors, and a measure of an animal's inhibin levels are most valuable when compared to the average inhibin levels of the same species of animal, of approximately the same age, at the same time of year if the animal has a breeding season.

As the amount of inhibin produced by a bird varies according to the above factors, relative amounts of inhibin are established below for different age categories of birds. Table 1 illustrates the variance of ratites such as emus and ostriches in their inhibin production dependent upon whether they are poor or good egg producers, and dependent upon the age of the ratite.

TABLE 1

| Age (Months) | Inhibin Level | Reproductive Potential |
| --- | --- | --- |
| 6–12 | >5 | Poor |
| 6–12 | 2–5 | Moderate |
| 6–12 | 0–1.5 | Good |
| 24+ | >7 | Poor |
| 24+ | 3–7 | Moderate |
| 24+ | 0–2.5 | Good |

In the above table, the inhibin level is relative to a standard pool value of 1 for female ratites averaging 50 to 60 eggs per breeding season, which is good, and a value of 7 for a pool of functionally non-producing female ratites which produce less than 5 eggs per season, which is poor.

Yet another aspect of the present invention is a method of producing animal antibodies directed against a class of another animal's antibodies, such as IgG. Briefly described, the method of producing antibodies in an animal which are directed against another animal's IgG, comprises the steps of: administering an effective amount of a class of a first animal's antibodies, such as those produced by the above described method, to a second animal such that an immunological response occurs in the second animal against the first animal's antibodies; withdrawing a blood sample from the second animal; and isolating the second animal's antibodies from the serum of the blood sample as described above. Preferably, the second animal is a different species than the first animal.

The present invention is also directed to a rapid, simple, reliable, cost-effective method for determining whether an animal has immunologically responded to a challenge with an inhibin composition. This method utilizes a second animal's antibodies directed against a class of antibodies from a first animal as described above. Briefly described, the method comprises binding inhibin or the heterologous protein of the present invention, to a solid phase, and contacting the immobilized inhibin with a sample of blood from the animal to be tested. The sample is contacted with the immobilized inhibin under conditions wherein the inhibin will selectively interact with any anti-inhibin antibodies in the sample. After removing uninteracted antibodies from the sample and washing, a quantity of labeled antibodies from a second animal which are directed against a class of the first animal's antibodies are added. The labeled antibodies which are directed against the animal antibodies will then selectively interact with the antibodies which are bound to the immobilized inhibin. After removal of the uninteracted labeled antibodies, the presence or quantity of interacted labeled antibodies is determined by visualizing the label. Thus, the method detects the presence of antibodies directed against inhibin in the animal, and therefore determines if the animal has immunologically responded to the administration of a composition comprising inhibin.

It is to be understood that the method of determining if an animal has immunologically responded to the administration of a composition comprising inhibin can be performed on a female animal of any species. The animal can be a bird, mammal, fish, or reptile, among others. More specifically, the mammal includes, but is not limited to, a cow, human, horse, cat, dog, sheep, mink, fox, otter, ferret, raccoon, and pig. The bird includes, but is not limited to, an ostrich, emu, a rhea, and chicken. A preferred animal is a bird. A more preferred animal is a ratite. An especially preferred animal is an ostrich. Another preferred animal is an emu. Yet another preferred animal is a rhea.

One of ordinary skill in the art will understand that the immunoassay techniques that can be used in the above method are well known in the art. Therefore, any immunoassay technique, label, and visualization method can be used in the above method. A preferred immunoassay is ELISA, and a preferred label is horseradish peroxidase. Another preferred label is a colored latex bead. The colored latex bead can be any color desired for visualization purposes. Preferably, the latex bead is yellow, red, blue, or green. The colored latex bead can be hollow or solid, but it preferably is hollow to minimize its weight. The size of the latex bead varies according to its intended use in immunoassays. One of ordinary skill in the art would be able to ascertain the largest bead size that is visible yet does not interfere stearically with the immunoassay reactions. Preferably, the latex bead is less than $0.5\mu$ in diameter, and most preferably it is less than $0.2\mu$ in diameter.

Another embodiment of the present invention is directed to the above method of determining if an animal has immunologically responded to the administration of a composition comprising inhibin wherein the immunoassay method is modified as follows. Briefly described, the method comprises obtaining a sample of blood from an animal, and contacting it with labeled animal inhibin, or a fragment thereof. The sample is contacted with the labeled animal inhibin under conditions wherein the animal inhibin will selectively interact with any anti-inhibin antibodies in the sample. After removing uninteracted labeled inhibin from the sample, the presence or quantity of interacted labeled inhibin is determined by visualizing the label. The inhibin used in this method is selected from, but is not limited to: the fused heterologous inhibin protein of the present invention; endogenous inhibin, or fragments thereof; and exogenous inhibin, or fragments thereof. Preferably, the labeled inhibin is endogenous inhibin.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Producing a fused gene product comprising a gene encoded for expressing chicken inhibin, and a gene encoded for expressing maltose binding protein.

The following is a method for producing a fused gene product comprising a gene ($cINA_{521}$) encoded for expressing a fragment of alpha-subunit chicken inhibin (SEQ ID NO:2), and a gene encoded for expressing maltose binding protein. The fused gene product of the present invention is made from the pMAL™-c vector kit, from New England Biolabs, Beverly, Mass.

The pMAL™ vectors provide a method for producing a protein expressed from a gene cloned in a reading frame. The cloned gene is inserted downstream from a gene, which encodes maltose-binding protein ("MBP"), and results in the expression of an MBP fusion protein ("MBP-$cINA_{521}$"). The method yields high-level expression of the cloned sequences, and a one-step purification for the fusion protein, MBP-$cINA_{521}$, using MBP's affinity for maltose.

The following is a Method of Ligating the Inhibin Gene, $cINA_{521}$, into a pMAL™-c Vector:

1. Digest 0.5 µg pMAL™-c plasmid DNA in 20 µl with the restriction endonuclease Pst1.
2. Digest 5 µg of cINA6 plasmid DNA which contains the chicken inhibin gene with the same enzyme, Pst1.
3. Check for complete digestion by running 4 µl of the pMAL™ reaction and 4 µl of the cINA6 reaction on a 0.8% agarose gel. Then run preparative agarose gel and purify the Pst1 $cINA_{521}$ fragment by prep-A-Gene purification kit.
4. Add 0.05 Units of calf intestinal alkaline phosphatase (NEB #290) to the vector DNA digestion. Incubate at 37° C. for 1 hour.
5. Add an equal volume of a 1:1 phenol/chloroform mixture to the vector restriction digest, mix, and after centrifuging, remove the aqueous (top) phase and place in a fresh tube. Repeat with chloroform alone.
6. Add 10 µg glycogen or tRNA to the vector digest as carrier, add ⅒th volume 3M sodium acetate, mix, then add two volumes ethanol. Incubate at −20° C. for 30 minutes.
7. Microcentrifuge for 15 minutes. Pour off the supernatant, rinse the pellet with 70% ethanol, and allow to dry.
8. Resuspend each sample in 20 µl of water.
9. Mix: 0.2 µg vector digest; 0.5 µg insert digest; add water, up to 18 µl, then add 2 µl of 10× ligase buffer; 0.5 µl NEB T4 ligase (#202; ~200 units); and incubate at 16° C. for 2 hours to overnight.
10. Heat at 65° C. for 5 minutes; cool on ice.
11. Mix 5 µl of ligation mixture with 100 µl competent DH5α (or any lacZα-complementing strain) and incubate on ice for 15–30 minutes. Heat to 42° C. for 2 minutes.
12. Add 1 ml LB and incubate at 37° C. for 60 minutes. Spread on an LB plate containing 100 µg/ml ampicillin. Incubate overnight at 370° C. Pick colonies with a sterile toothpick onto a master LB amp plate and an LB amp plate containing 80 µg/ml Xgal and 0.1 mM IPTG. Incubate at 37° C. for 8 to 16 hours. Score the Lac phenotype on the Xgal plate and recover the "white" clones from the master.
13. Screen for the presence of inserts in one or both of the following ways:
    A. Prepare miniprep DNA. Digest with an appropriate restriction endonuclease to determine the presence and orientation of the insert.
    B. i) Grow a 5 ml culture in LB amp broth to about $2\times10^8$/ml.
        ii) Take a 1 ml sample. Microcentrifuge for 2 minutes, discard the supernatant and resuspend the cells in 50 µl protein gel SDS-PAGE sample buffer.
        iii) Add IPTG to the remaining culture to 0.3 mM, for example 15 µl of a 0.1M stock solution. Incubate at 37° C. with good aeration for 2 hours.

iv) Take a 0.5 ml sample. Microcentrifuge for 2 minutes, discard the supernatant and resuspend the cells in 100 µl SDS-PAGE sample buffer.

v) Boil the samples 5 minutes. Electrophorese 15 µl of each sample on a 10% SDS-PAGE gel along with a set of protein MW standards and 15 µl of the supplied MBP in SDS-PAGE sample buffer. Stain the gel with Coomassie brilliant blue. An induced band is easily visible at a position corresponding to the molecular weight of the fusion protein. The molecular weight of the MBP alone is 42,000 Daltons.

EXAMPLE 2

Producing a fused heterologous protein, "MBP-cINA$_{521}$", comprising chicken inhibin and maltose binding protein.

The following is a method of producing a fused heterologous protein comprising chicken inhibin and maltose binding protein, "MBP-cINA$_{521}$". The fused gene product of Example 1 expresses the fused heterologous maltose binding protein-inhibin protein, "MBP-cINA$_{521}$", as follows:

1. Inoculate 80 ml rich broth+glucose and ampicillin (see Media and Solutions below) with 0.8 ml of an overnight culture of cells containing the fusion plasmid of Example 1.
2. Grow at 37° C. with good aeration to $2\times10^8$ cells/ml ($A_{600}$ of ~0.5). Take a sample of 1 ml and Microcentrifuge for 2 minutes (uninduced cells). Discard supernatant and resuspend the cells in 50 µl SDS-PAGE sample buffer. Vortex and place on ice.
3. Add IPTG (isopropylthiogalactoside) to the remaining culture to give a final concentration of 0.3 mM, e.g. 0.24 ml of a 0.1M stock in H$_2$O (see Media and Solutions). Continue incubation at 37° C. for 2 hours. Take a 0.5 ml sample and microcentrifuge for two minutes (induced cells). Discard supernatant and resuspend the cells in 100 µl SDS-PAGE: sample buffer. Vortex to resuspend cells and place on ice.
4. Divide the culture into two aliquots. Harvest the cells by centrifugation at 4000 xg for 10 min. Discard the supernatant and resuspend one pellet (sample A) in 5 ml of lysis buffer (see Media and Solutions). Resuspend the other pellet (sample B) in 10 ml 30 mM Tris-Cl, 20% sucrose, pH 8.0 (8 ml for each 0.1 g cells wet weight).
5. Freeze samples in a dry ice-ethanol bath (or overnight at −28° C.). Thaw in cold water (20° C. is more effective than 70° C., but takes longer).
6. Sonicate, monitor cell breakage, by measuring the release of protein using the Bradford assay or the release of nucleic acid at $A_{260}$, until it reaches a maximum. Add 0.6 ml 5M NACl.
7. Centrifuge at 9,000 × g for 20 minutes. Decant the supernatant (crude extract 1) and save on ice. Resuspend the pellet in 5 ml lysis buffer. This is a suspension of the insoluble matter (crude extract 2).

Column Purification of heterologous fused maltose binding protein-inhibin protein, "MBP-cINA$_{521}$" as produced above, is as follows:

1. Swell amylose resin (1.5 g) for 30 min. in 50 ml column buffer (see Media and Solutions) in a 250 ml filter flask. De-gas with an aspirator. Pour in a 2.5×10 cm column. Wash the column with 3 column volumes of the same buffer +0.25% Tween 20. The amount of resin needed depends on the amount of fusion protein produced. The resin binds about 3 mg/ml bed volume, so a column of about 15 ml should be sufficient for a yield of up to 45 mg fusion protein/liter culture. A 50 ml syringe plugged with silanized glass wool can be substituted for the 2.5 cm column. The column height to diameter ratio should be less than or equal to 4.

2. Dilute the crude extract 1:5 with column buffer+0.25% Tween 20. Load the diluted crude extract at a flow rate of [10× (diameter of column in cm)$^2$]ml/hr. This is about 1 ml/min. for a 2.5 cm column. The dilution of the crude extract is aimed at reducing the protein concentration to about 2.5 mg/ml. If the crude extract is less concentrated, do not dilute it as much. A good rule of thumb is that 1 g wet weight of cells gives about 120 mg protein.

3. Wash with 2 column volumes column buffer+0.25% Tween 20.

4. Wash with 3 column volumes column buffer without Tween 20.

5. Elute the fusion protein, "MBP-cINA$_{521}$", with column buffer+10 mM maltose+0.1% SDS (optional 10 mM β-mercaptoethanol, 1 mM EGTA). Collect 10–20 3 ml fractions. Assay the fractions for protein, e.g., by the Bradford assay or $A_{260}$; the fractions containing the fusion protein have easily detectable protein. The fusion protein elutes soon after the void volume of the column.

Media and Solutions

* Rich medium+glucose and ampicillin=per liter: 10 g tryplone, 5 g yeast extract, 5 g NaCl, 2 g glucose. Autoclave; add sterile ampicillin to 100 µg/ml.

* 0.1M IPTG Stock=1.41 g IPTG (isopropyl-β-o-thiogalactoside); add H$_2$O to 50 ml. Filter, and sterilize.

* 0.5M sodium phosphate buffer, pH 7.2 (stock)=
(A) 69.0 g NaH$_2$PO$_4$H$_2$O to 1 liter with H$_2$O.
(B) 70.9 g Na$_2$HPO$_4$ to 1 liter with H$_2$O.

Mix 117 ml (A) with 383 ml (B). The pH of this stock should be ~7.2. Diluted to 10 mM in column buffer, the pH should be 7.0.

| Per Liter | Final Concentration |
| --- | --- |
| Lysis Buffer | |
| 20 ml 0.5M Na$_2$HPO$_4$ | 10 mM phosphate |
| 1.75 g NaCl | 30 mM NaCl |
| 10 ml 25% Tween 20 | 0.25% Tween j20 |
| 0.7 ml β-mercaploethanol ("β-ME") (optional) | 10 mM β-ME |
| 20 ml 0.5M EDTA (pH 8) | 10 mM EDTA |
| 10 ml 1M EGTA (pH 7) | 10 mM EGTA |
| Adjust to pH 7.0 with HCL or NaOH | |
| Column Buffer | |
| 20 ml 0.5M sodium phosphate, pH 7.2 | 10 mM phosphate |
| 29.2 g NaCl | 0.5M NaCl |
| 1 ml 1M sodium azide | 1 mM azide |
| 0.7 mM β-ME (optional) | 10 mM β-ME |
| 1 ml 1M EGTA (pH 7) (optional) | 1 mM EGTA |
| Adjust to pH 7.0 if necessary. | |
| Low Salt Column Buffer | |
| 20 ml 0.5M sodium phosphate, pH 7.2 | 10 mM phosphate |
| 1.75 g NaCl | 30 mM NaCl |
| 1 ml 1M sodium azide | 1 mM azide |
| 0.7 ml β-mercaptoethanol (optional) | 10 mM β-ME |
| 1 ml 1M EGTA (pH 7) (optional) | 1 mM EGTA |
| Adjust to pH 7.0 if necessary. | |

The purity of the fused chicken inhibin-MBP heterologous protein, "MBP-cINA$_{521}$", after passing through the column is illustrated in FIG. 1, columns "E". The column marked "F" is the eluent from the column when no heterologous protein has been loaded on the column (the negative control). The columns marked "B" represent the plasmid pMAL™-c vector standards. The columns marked "C" are molecular weight standards. The columns marked "D" are the actual pMAL™-c vector used in the preparation of the fused chicken-inhibin-MBP heterologous protein, "MBP-cINA$_{521}$", prior to the insertion of the inkibin gene as described in Example 2. The above proteins were electrophoresed on a SDS-PAGE gel in SDS-PAGE sample buffer, and stained with Coomassie brilliant blue stain.

EXAMPLE 3

Immunizing an Ostrich against Inhibin.

The following is a method for immunizing an ostrich against inhibin. A primary immunization is administered to the ostrich approximately six months prior to the bird's first breeding season, and then booster immunizations are administered at one month intervals for six months. Accordingly, it is preferable to administer the primary immunization to an ostrich when it is between approximately 18 and 24 months old. The primary immunization comprises between approximately 1.5 to 3.0 mg of a fused heterologous protein comprising chicken inhibin (a fragment of the alpha subunit) and maltose binding protein produced by the methods described in Examples 1 and 2. The booster immunizations comprise between approximately 0.75 to 1.5 mg of the fused heterologous protein. The fused heterologous protein is emulsified in Freund's Complete Adjuvant (Sigma Chemical Co., St. Louis, Mo.) in the primary immunization, and the fused heterologous protein is emulsified in Freund's Incomplete Adjuvant (Sigma) in the booster immunizations. The fused heterologous protein composition is injected subcutaneously at three sites along the upper thigh region of the ostrich.

EXAMPLE 4

Producing Ostrich Antibodies Selectively Directed Against Inhibin.

The following is a method of producing ostrich antibodies ("ostrich anti-chicken inhibin antibodies") which are selectively directed against a heterologous protein of the present invention comprising chicken inhibin and maltose binding protein. More particularly, the ostrich antibodies are IgG antibodies. The heterologous protein used is a fused protein comprising chicken inhibin and maltose binding protein produced by the methods described in Examples 1 and 2. To produce the antibodies, immunize an ostrich with chicken inhibin-MBP heterologous protein according the method described in Example 3. The amount administered to the ostrich must be sufficient to ellicit an immunological response in the ostrich against the heterologous protein. Withdraw approximately 5 ml of blood from the ostrich, and then isolate antibodies directed against inhibin from the remainder of the blood sample. Any separation method known in the art can be used to isolate the antibodies. Preferably, standard ELISA techniques are employed in conjunction with affinity and HPLC columns.

EXAMPLE 5

Producing Goat Antibodies Selectively Directed Against Ostrich Antibodies.

The following is a method of producing goat antibodies which are selectively directed against a class of ostrich antibodies, including the antibodies produced in Example 4, more particularly IgG ostrich antibodies. In this method a goat is immunized with 0.5 to 3.0 mg ostrich IgG such that an immunological response occurs in the goat against the ostrich IgG. The ostrich IgG are obtained from a pool of sera from different ostriches. Blood is obtained from the goat, and goat anti-ostrich IgG is then isolated from the sample using standard techniques that are well known in the art.

The pool of sera is purified using standard methods that involve precipitation using 50% ammonium sulfate, and subsequent fractionation using a protein-A sepharose column. Preferably, the IgG precipitation is conducted as follows. Twelve milliliters of sera containing IgG is diluted 1:1 with 50 mM-Tris (pH 8.0). Next, 24 ml of saturated ammonium sulphate is added slowly with stirring (all at 4° C.), and the mixture is stirred for approximately 2 hours. Centrifuge the mixture at 10,000 rpm for 10 minutes to collect the precipitate. Resuspend the precipitate in 50 mM-Tris/Saline (to 12 ml), and dialyse overnight versus 2 L of 50 mM-Tris at 4° C., the final volume being 20 ml.

Preferably, the subsequent fractionation using a protein-A sepharose column is as follows. The column contains protein-A sepharose CL-4B (Pharmacia Biotech, Inc., Piscataway, N.J.). The column is loaded with approximately 5 ml of ammonium sulfate/serum precipitate. The sample is allowed to bind to the protein A-sepharose for approximately 30 minutes. Next, the column is washed with 0.1M phosphate buffer (pH 7.5), and the absorbed IgG is eluted with 0.1M Glycine (pH 2.8). Finally, the eluted fractions are neutralized by adding a few drops of 1M Tris-HCl (pH 9). The quality of the purified ostrich IgG is tested by visualization after SDS-polyacrylamide gel electrophoresis before it is administered to a goat.

The method of immunization and the adjuvants used are not critical to the invention, thus any method known in the art can be used, and any adjuvant system known in the art can be used. Preferably, the purified ostrich IgG will be injected into a goat subcutaneously. It is also preferable to administer boost injections at four week intervals using Freund's incomplete adjuvant. Preferably, the purified IgG will be administered with Freund's Complete Adjuvant or Hunter's Titermax (Sigma Chemical Co., St. Louis, Mo.). A goat develops a satisfactory immune response after three to four injections.

Next, 5–10 ml of blood is withdrawn from the goat, and the goat antibodies directed against ostrich IgG are isolated from the blood sample. Any method known in the art can be used to separate the goat antibodies from the blood sample. A preferred method for separating the goat antibodies from the sample is by passing the blood sample through an ostrich IgG column. The goat antibodies are then collected from the column by washing the column with glycine buffer-pH 8.0.

EXAMPLE 6

Monitoring The Immunological Response Of An Ostrich After Its Vaccination With A Fused Heterologous Protein.

The following is a method of monitoring the immunological response of an ostrich after it has been vaccinated with a fused heterologous protein comprised of chicken inhibin and maltose binding protein produced by the method of Examples 1 and 2, wherein the immunological response is monitored using the goat antibodies produced in Example 5. To determine whether an ostrich has immunologically reacted to the fused inhibin-MBP heterologous protein, first bind the heterologous protein to a solid phase. Next, withdraw 5–10 ml of blood from an ostrich that has been immunized with the heterologous protein, and isolate the serum from the blood. Contact the immobilized heterologous protein with the serum under conditions wherein the heterologous protein will selectively interact with any anti-inhibin antibodies in the serum. After washing, add the goat antibodies produced in Example 5 which have been labeled with HRP. The labeled goat antibodies will then selectively interact with the ostrich antibodies which are bound to the immobilized heterologous protein. After the removal of the uninteracted labeled antibodies, the presence or quantity of interacted HRP labeled goat antibodies is determined by visualizing the label. Preferably, the label is visualized by adding Nitro Blue Tetrazolium ("NBT"), a substrate to HRP.

One of ordinary skill in the art will understand that the immunoassay techniques that are used in the above method are well known in the art. Therefore, any immunoassay technique, label, and visualization method can be used in the above method. A preferable immunoassay is ELISA, and a preferable label is horseradish peroxidase. Another preferable label is a colored latex bead.

EXAMPLE 7

Determining The Reproductive Potential Of An Ostrich.

The following is a method for determining the reproductive potential of an ostrich by quantifying the amount of inhibin in the ostrich's blood. Circulating inhibin concentrations in the blood of an ostrich can be determined using radioimmunoassay (RIA) or standard sandwich ELISA techniques. First, bind the anti-inhibin antibodies produced in Example 4, to the wells of a microtiter plate. After washing and blocking the plate, then add a quantity of blood plasma or serum that was obtained from the ostrich to a well of the microtiter plate. After allowing any inhibin in the sample, if present, to selectively interact with the immobilized anti-inhibin antibodies, the sample is washed from the well of the plate. Next, add a different anti-inhibin antibody to the well than that produced in Example 4, which is conjugated with horseradish peroxidase. The HRP conjugated anti-inhibin antibody differs from the immobilized anti-inhibin body in that they are selectively directed against different portions of inhibin. After allowing the labeled anti-inhibin antibody to selectively interact with any immobilized inhibin, any uninteracted labeled anti-inhibin antibodies are removed by washing. The amount of inhibin present in the plasma sample is determined by adding NBT to the well and visualizing the amount of immobilized labeled anti-inhibin antibody in the well. Standard positive and negative controls are run simultaneously in neighboring plate wells. Many immunoassay techniques, labels and visualization methods are well known in the art. Accordingly, any immunoassay method, label, and visualization technique can be used in the present invention.

EXAMPLE 8

Enhancing Egg Production In Quail

As stated above, the chicken inhibin a-subunit cDNA clone (cINA6) inserted into the EcoR 1 site of Bluescript was obtained as a gift of P. A. Johnson (Cornell University). A DNA fragment ("cINA521") was excised from the cINA6 clone using Pst I digestion. The $cINA_{521}$ DNA fragment encompassed most of the mature chicken inhibin α-subunit. This fragment ($cINA_{521}$) was cloned in plasmid p-MAL™-c in frame with the maltose binding protein ("MBP") and a fusion protein of appropriate size (Lane E; FIG. 1) was detected after IPTG (isopropyl β-D-thiogalactopyranoside) induction and SDS-PAGE. The resulting protein conjugate ("MBP-$cINA_{521}$") was used as an antigen to immunize pre-pubescent, female Japanese quail (Coturnix coturnix japonica) against circulating inkibin levels as described below.

Hatchling quail were brooded in a Model 2S-D Petersime brooder battery modified for quail. Initial brooding temperature was approximately 37.8° C. with a weekly decline of approximately 2.8° C. until ambient temperature was achieved. During the growing period (i.e., until approximately 6 wks-of-age), a quail starter ration (28% CP, 2,800 kcal ME/kg of feed) and water were provided for ad libitum consumption, and continuous dim light (22 1x) with a 14 h light (280 to 300 1x):10 hr dark override was used. At 25 days-of-age, 50 quail were randomly and equally assigned to one of two injection groups (25 birds per group) as follows: (1) MBP-$cINA_{521}$ in Freund's adjuvant ("MBP-cINA521/FRN"), or (2) Freund's (adjuvant control; "FRN"). Birds immunized against inhibin (Group 1) were given approximately 0.75 mg MBP-$cINA_{521}$ per bird in the appropriate control vehicle. Equivalent vehicular injection volumes (0.2 mL) of FRN were administered to Group 2. All injections were given subcutaneously using tuberculin syringes fitted with 25 ga needles. Following the initial injections, quail were wingbanded to identify them by treatment before housing (individually) in laying cages. Weekly booster inhibin immunizations of approximately 0.375 mg MBP-$cINA_{521}$ per bird, or appropriate control challenges, were subsequently administered for five consecutive weeks (i.e., at 32, 39, 46, 53, and 60 days-of-age) and then every 35 days thereafter for three additional challenges (i.e., at 95, 130, and 165 days-of-age). Beginning at 6 weeks-of-age, a quail breeder ration (21% CP, 2,750 kcal ME/kg of feed) and water were provided for a d libitum consumption.

Beginning at 41 days-of age (considered Day 1 of the egg lay cycle), daily hen-day egg production ("HDEP") and mortality ("MORT") measures were recorded for 20 consecutive weeks. In addition, average age at first egg lay ("FIRST") and age at which hens reached 50% egg production ("FIFTY"), or maximum egg lay as defined above, were calculated for each of the treatment groups.

Hen-day egg production data were subjected to an analyses of variance ("ANOVA") of which incorporated a completely randomized design with a split-plot arrangement of treatments. The main plot consisted of the two injection treatments (MBP-$cINA_{521}$/FRN, or FRN) and the 20 laying periods of 7 days each comprised the split.

Inhibin immunoneutralization clearly accelerated puberty in the quail hens. The average age of FIRST egg lay was decreased (P<0.0088) by nearly six days in inhibin-treated hens (Table 2). Likewise, the age to FIFTY egg production was markedly reduced (12 days; P<0.01) in inhibin-treated hens (Table 3).

A positive effect of inhibin treatment on hen day egg production (HDEP) was also extant, most notably at the beginning and at the end of the laying cycle (FIG. 2). For example, significantly greater (P<0.05) mean HDEP rates were observed in hens treated with MBP-$cINA_{521}$/FRN when compared to the FRN controls during Weeks 1 (16.5 vs 2.6%), 2 (50.0 vs 28.6%), and 4 (96.6 vs 79.7%) and again during Weeks 15 (98.8 vs 86.9%), 16 (96.9 vs 86.3%), 18 (85.7 vs 66.1%), and 20 (96.8% vs 73.8%). Total HDEP rate (inclusive of all 20 weeks of lay) for inhibin-treated hens was 83.5% as compared to 75.4% for the controls.

Besides accelerating puberty, prolonging egg lay, and enhancing the overall intensity of lay, inhibin-treatment decreased the time needed to reach peak egg lay by approximately 3 weeks (FIG. 2; Compare MBP-$cINA_{521}$/FRN=

96.6% HDEP by Week 4 vs FRN=96.6% HDEP by Week 7). Although differences in peak HDEP values were not statistically evaluated, the treatment differences in mean age at which hens reached 50% HDEP levels (FIFTY) reflect peak performance.

Mortality was not a factor in this study as only eight birds have died (three controls, five treated). Such MORT (16%) would be within expected limits for quail that have reached 180 days-of-age.

TABLE 2

Effect of inhibin immunoneutralization on mean (±SE) age at first egg lay in Japanese quail

| Treatment | Age at first egg lay (days) |
|---|---|
| FRN[1] | 56.15 ± 1.82[a] |
| MBP-cINA$_{521}$/FRN[2] | 50.38 ± 1.08[b] |

[1]= Freund's adjuvant control.
[2]= MBP-cINA$_{521}$/FRN = Maltose Binding Protein-chicken $\alpha_{515}$-inhibin fusion protein in Freund's adjuvant.
[a,b]($p < .0088$).

TABLE 3

Effect of inhibin immunoneutralization on mean (±SE) age at 50% egg production in Japanese quail

| Treatment | Age at 50% egg production (days) |
|---|---|
| FRN[1] | 73.04 ± 3.78[a] |
| MBP-cINA$_{521}$/FRN[2] | 61.00 ± 2.70[b] |

[1]= Freund's adjuvant control.
[2]= MBP-cINA$_{521}$/FRN = Maltose Binding Protein-chicken $\alpha_{515}$-inhibin fusion protein in Freund's adjuvant.
[a,b]($p < .01$).

Incidences of shelless (unshelled) and thin-shelled eggs occurred at greater frequencies in control birds, particularly during the latter stages of the laying cycle, than in inhibin-immunized birds. This suggests that greater numbers of defective eggs (i.e., eggs that were either unfit for consumption or likely to break before consumption, or unsettable as hatching eggs) were associated with the control treatment.

EXAMPLE 9

Enhancing Production Performance In Ostriches.

The protein conjugate (MBP-cINA$_{521}$) is used as an antigen to immunize prepubescent, female ostriches against circulating inhibin levels, and to therefore accelerate the onset of egg lay in the treated ostriches. The method described in Example 8 is followed with the following exceptions. The average age at puberty for untreated ostriches is between approximately 28 and 32 months. The following is the treatment schedule for ostriches having an approximate body weight range of 150 to 300 pounds: primary (first) injection of 5.0 mg of the heterologous protein of the present invention on its 26th month of age; and boosters of 2.5 mg on the 27th, 28th, 30th, 32nd, 34th, and 36th month of age.

EXAMPLE 10

Enhancing Production Performance In Emu.

The protein conjugate (MBP-cINA$_{521}$) is used as an antigen to immunize prepubescent, female emu against circulating inhibin levels, and to therefore accelerate the onset of egg lay in the treated emu. The method described in Example 8 is followed with the following exceptions. The average age at puberty for untreated emu is approximately 20 months. The following is the treatment schedule for emu having an approximate body weight range of 50 to 90 pounds: primary (first) injection of 3.0 mg of the heterologous protein of the present invention on its 18th month of age; and boosters of 1.5 mg on the 19th, 20th, 22nd, 24th, 26th, and 30th month of age.

EXAMPLE 11

Enhancing Production Performance In Chickens.

The protein conjugate (MBP-cINA$_{521}$) is used as an antigen to immunize prepubescent, female chickens against circulating inhibin levels, and to therefore accelerate the onset of egg lay in the treated chickens. The method described in Example 8 is followed with the following exceptions. The average age at puberty for an untreated chicken is approximately 20 weeks. The following is the treatment schedule for a chicken having an approximate body weight range of 2.0 to 3.5 pounds: primary (first) injection of 1.5 mg of the heterologous protein of the present invention on its 15th week of age; and boosters of 0.75 mg on the 17th, 20th, 24th, 30th, 40th, and 50th week of age.

EXAMPLE 12

Enhancing Production Performance In Turkeys.

The protein conjugate (MBP-cINA$_{521}$) is used as an antigen to immunize prepubescent, female turkeys against circulating inhibin levels, and to therefore accelerate the onset of egg lay in the treated turkeys. The method described in Example 8 is followed with the following exceptions. The average age at puberty for an untreated turkey is approximately 30 weeks. The following is the treatment schedule for a turkey having an approximate body weight range of 9.0 to 12 pounds: primary (first) injection of 2.0 mg of the heterologous protein of the present invention on its 28th week of age; and boosters of 1.0 mg on the 29th, 30th, 34th, 38th, 46th, and 54th week of age.

EXAMPLE 13

Enhancing Production Performance In Parrots.

The protein conjugate (MBP-cINA$_{521}$) is used as an antigen to immunize prepubescent, female parrots against circulating inhibin levels, and to therefore accelerate the onset of egg lay in the treated parrots. The method described in Example 8 is followed with the following exceptions. The average age at puberty for an untreated parrot is approximately 30 months. The following is the treatment schedule for a parrot having an approximate body weight range of 0.5 to 1.25 pounds: primary (first) injection of 0.75 mg of the heterologous protein of the present invention on its 28th month of age; and boosters of 0.375 mg on the 29th, 30th, 32nd, 34th, 36th, and 38th month of age.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method which increases egg lay, accelerates onset of egg lay, accelerates onset of maximum egg lay, increases lifetime total egg lay, increases egg production, increases intensity of egg production, prolongs persistence of egg lay, improves egg shell quality, accelerates onset of puberty, accelerates onset of ovulation, prolongs persistence of ovulation, increases sperm production, accelerates onset of sperm production, accelerates onset of maximum sperm production, prolongs persistence of sperm production, improves sperm viability, increases testosterone production, increases ejaculate volume, or increases libido, of a bird, comprising administering an effective mount of a heterologous protein comprising avian alpha-subunit inhibin protein, or an immunogenic fragment thereof, and a carrier protein, to the bird.

2. The method of claim 1, wherein the bird is selected from the group consisting of ratites, psittaciformes, falconiformes, piciformes, strigiformes, passeriformes, coraciformes, ralliformes, cuculiformes, columbiformes, galliformes, anseriformes, and herodiones.

3. The method of claim 2, wherein the ratite is an ostrich, emu, rhea, kiwi, or cassowary.

4. The method of claim 2, wherein the bird is a chicken, turkey, parrot, parakeet, macaw, falcon, eagle, quail, hawk, pigeon, cockatoo, song bird, jay bird, blackbird, finch, warbler, goose, duck, canary, mynah, toucan, or sparrow.

5. The method of claim 1, wherein the carrier protein is maltose binding protein, bovine serum albumin, ovalbumin, flagellin, keyhole-limpet hemocyanin, thyroglobulin, serum albumin, gamma globulin, or polymers of amino acids.

6. The method of claim 1, wherein the bird is a female bird.

7. The method of claim 1, wherein the bird is a male bird.

8. The method of claim 1, wherein the administration of the heterologous protein increases egg production.

9. The method of claim 8, wherein the bird is a quail, turkey, chicken, parrot or ratite.

10. The method of claim 1, wherein the administration of an effective amount of the heterologous protein comprises administration of approximately 0.1 mg to 10.0 mg of heterologous protein to the bird.

11. The method of claim 1, wherein the administration of an effective amount of the heterologous protein comprises administration of approximately 0.1 mg to 6.0 mg of the heterologous protein to the bird.

12. The method of claim 1, further comprising administration of one or more booster injections of approximately 0.05 mg to 5.0 mg of the heterologous protein.

13. The method of claim 1, further comprising administration of one or more booster injections of approximately 0.05 mg to 2.0 mg of the heterologous protein.

14. The method of claim 1, wherein the administration of the heterologous protein occurs before puberty.

15. The method of claim 1, wherein the administration of the heterologous protein occurs during puberty.

16. The method of claim 1, wherein the heterologous protein is a fused heterologous protein.

17. The method of claim 1, wherein the heterologous protein is a conjugated heterologous protein.

18. The method of claim 1, further comprising administration of adjuvants, preservatives, diluents, emulsifiers, or stabilizers.

19. The method of claim 1, wherein the administration occurs after puberty.

20. The method of claim 1, wherein the avian alpha-subunit inhibin protein, or an immunogenic fragment thereof, comprises the amino acid sequence set forth in SEQ ID NO:2.

* * * * *

UNITED STATES PATENT AND TRADEMARK OFFICE
CERTIFICATE OF CORRECTION

Page 1 of 2

PATENT NO. : 5,725,858

DATED : March 10, 1998

INVENTOR(S) : FIORETTI ET AL.

It is certified that error appears in the above-identified patent and that said Letters Patent is hereby corrected as shown below:

At column 12, line 2, please delete "Mother" and insert therefor --Another--.
At column 15, line 42, please delete "Of" and insert therefor --of--.
At column 16, line 42, please delete "inkibin" and insert therefor --inhibin--.
At column 17, line 28, please delete "798" and insert therefor --797--.
At column 24, line 57, please delete "melted" and insert therefor --molted--.
At column 28, line 19, please delete "non-vital" and insert therefor --non-viral--.
At column 28, line 44, please delete "vitally" and insert therefor --virally--.
At column 30, line 45, please delete "carded" and insert therefor --carried--.
At column 30, line 54, please delete "carded" and insert therefor --carried--.
At column 32, line 67, please delete "mount" and insert therefor --amount--.
At column 33, line 15, please delete "an" and insert therefor --art--.

UNITED STATES PATENT AND TRADEMARK OFFICE
CERTIFICATE OF CORRECTION

PATENT NO. : 5,725,858
DATED : March 10, 1998
INVENTOR(S) :
FIORETTI ET AL.

It is certified that error appears in the above-identified patent and that said Letters Patent is hereby corrected as shown below:

At column 39, line 8, please delete "inkibin" and insert therefor --inhibin--.
At column 41, line 25, please delete "inbibin" and insert therefor --inhibin--.
At column 42, line 2, please delete "inkibin" and insert therefor --inhibin--.

In Claim 1, at column 47, line 58, please delete "mount" and insert therefor -- amount --.

Signed and Sealed this

Ninth Day of March, 1999

Attest:

Q. TODD DICKINSON

*Attesting Officer*   *Acting Commissioner of Patents and Trademarks*